US009507047B1

(12) United States Patent
Dvorkin et al.

(10) Patent No.: US 9,507,047 B1
(45) Date of Patent: Nov. 29, 2016

(54) METHOD AND SYSTEM FOR INTEGRATING LOGGING TOOL DATA AND DIGITAL ROCK PHYSICS TO ESTIMATE ROCK FORMATION PROPERTIES

(75) Inventors: Jack Dvorkin, Houston, TX (US); Henrique Tono, Houston, TX (US); Carl Sisk, Houston, TX (US); David Malone, Houston, TX (US)

(73) Assignee: Ingrain, Inc., Houston, TX (US)

( * ) Notice: Subject to any disclaimer, the term of this patent is extended or adjusted under 35 U.S.C. 154(b) by 1214 days.

(21) Appl. No.: 13/465,105

(22) Filed: May 7, 2012

Related U.S. Application Data

(60) Provisional application No. 61/484,254, filed on May 10, 2011.

(51) Int. Cl.
*G01V 5/10* (2006.01)

(52) U.S. Cl.
CPC ............... *G01V 5/101* (2013.01); *G01V 5/104* (2013.01); *G01V 5/107* (2013.01)

(58) Field of Classification Search
CPC .......... G01V 1/40; G01V 1/28; G01V 5/101; G01V 5/104; G06T 7/0004
See application file for complete search history.

(56) References Cited

U.S. PATENT DOCUMENTS

| | | | |
|---|---|---|---|
| 4,745,802 A | 5/1988 | Purfurst | |
| 5,055,787 A | 10/1991 | Kleinberg et al. | |
| 5,055,788 A | 10/1991 | Kleinberg et al. | |
| 5,167,149 A | 12/1992 | Mullins et al. | |
| 5,201,220 A | 4/1993 | Mullins et al. | |
| 5,247,830 A | 9/1993 | Goode | |
| 5,331,156 A | 7/1994 | Hines et al. | |
| 5,859,430 A | 1/1999 | Mullins et al. | |
| 5,912,459 A | 6/1999 | Mullins et al. | |
| 5,939,717 A | 8/1999 | Mullins | |
| 6,023,340 A | 2/2000 | Wu et al. | |
| 6,047,239 A | 4/2000 | Berger et al. | |
| 6,075,611 A | 6/2000 | Dussan et al. | |
| 6,111,408 A | 8/2000 | Blades et al. | |
| 6,140,637 A | 10/2000 | Mullins et al. | |
| 6,140,817 A | 10/2000 | Flaum et al. | |
| 6,268,603 B1 | 7/2001 | Mullins et al. | |
| 6,274,865 B1 | 8/2001 | Schroer et al. | |
| 6,346,813 B1 | 2/2002 | Kleinberg | |
| 6,350,986 B1 | 2/2002 | Mullins et al. | |
| 6,437,326 B1 | 8/2002 | Yamate et al. | |

(Continued)

OTHER PUBLICATIONS

Rothman, D., et al., Lattice-Gas Cellular Automata. Cambridge, UK: Cambridge University Press, 1997, pp. 155-157.

*Primary Examiner* — Manuel Rivera Vargas
(74) *Attorney, Agent, or Firm* — Kilyk & Bowersox, P.L.L.C.

(57) ABSTRACT

The present invention relates to a method and system for integrating logging tool data and digital rock physics to estimate rock formation properties. A rock sample from a logging tool such as a sidewall plug or large enough cutting can be extracted by the logging tool at approximately the same well bore location that the logging tool measures fluid properties. The rock samples thus obtained is scanned using a CT scanner, scanning electron microscope or other suitable scanning device. The resulting scanned rock image can be segmented and rock properties comprising porosity, absolute permeability, relative permeability, capillary pressure and other relevant rock properties are calculated. The resulting digital calculations are integrated with logging tool data and rock property estimates to improve the accuracy and timeliness of the logging tool data.

20 Claims, 22 Drawing Sheets

(56) References Cited

U.S. PATENT DOCUMENTS

| | | |
|---|---|---|
| 6,465,775 B2 | 10/2002 | Mullins et al. |
| 6,474,152 B1 | 11/2002 | Mullins et al. |
| 6,476,384 B1 | 11/2002 | Mullins et al. |
| 6,518,758 B1 | 2/2003 | Speier et al. |
| 6,528,995 B1 | 3/2003 | Speier et al. |
| 6,531,869 B1 | 3/2003 | Speier et al. |
| 6,538,438 B1 | 3/2003 | Speier et al. |
| 6,642,715 B2 | 11/2003 | Speier et al. |
| 6,691,037 B1 | 2/2004 | Poe et al. |
| 6,704,109 B2 | 3/2004 | Wu et al. |
| 6,710,596 B2 | 3/2004 | Speier et al. |
| 6,765,380 B2 | 7/2004 | Freedman et al. |
| 6,768,105 B2 | 7/2004 | Mullins et al. |
| 6,825,657 B2 | 11/2004 | Kleinberg et al. |
| 6,850,317 B2 | 2/2005 | Mullins et al. |
| 6,856,132 B2 | 2/2005 | Appel et al. |
| 6,891,369 B2 | 5/2005 | Hurlimann et al. |
| 6,992,768 B2 | 1/2006 | Dong et al. |
| 6,995,360 B2 | 2/2006 | Jones et al. |
| 7,075,062 B2 | 7/2006 | Chen et al. |
| 7,081,615 B2 | 7/2006 | Betancourt et al. |
| 7,095,012 B2 | 8/2006 | Fujisawa et al. |
| 7,142,306 B2 | 11/2006 | Wu et al. |
| 7,180,288 B2 | 2/2007 | Scheven |
| 7,191,831 B2 | 3/2007 | Reid et al. |
| 7,215,416 B2 | 5/2007 | Yamate et al. |
| 7,277,796 B2 | 10/2007 | Kuchuk et al. |
| 7,301,339 B1 | 11/2007 | Cheng et al. |
| 7,305,306 B2 | 12/2007 | Venkataramanan et al. |
| 7,339,160 B2 | 3/2008 | Raghuraman et al. |
| 7,398,159 B2 | 7/2008 | Venkataramanan et al. |
| 7,432,109 B2 | 10/2008 | Raghuraman et al. |
| 7,445,043 B2 | 11/2008 | Mullins et al. |
| 7,458,258 B2 | 12/2008 | Xian et al. |
| 7,461,547 B2 | 12/2008 | Terabayashi et al. |
| 7,500,388 B2 | 3/2009 | Fujisawa et al. |
| 7,542,142 B2 | 6/2009 | Wu et al. |
| 7,644,611 B2 | 1/2010 | Kamiya et al. |
| 7,652,950 B2 | 1/2010 | Sinha et al. |
| 7,687,769 B2 | 3/2010 | Indo et al. |
| 7,687,770 B2 | 3/2010 | Indo et al. |
| 7,705,982 B2 | 4/2010 | Triana et al. |
| 7,733,490 B2 | 6/2010 | Goodwin et al. |
| 7,757,760 B2 | 7/2010 | Sherwood et al. |
| 7,788,972 B2 | 9/2010 | Terabayashi et al. |
| 7,822,554 B2 | 10/2010 | Zuo et al. |
| 2006/0283606 A1 | 12/2006 | Partouche et al. |
| 2008/0136410 A1 | 6/2008 | Song et al. |
| 2009/0025926 A1 | 1/2009 | Briquet et al. |
| 2009/0078036 A1 | 3/2009 | Terabayashi et al. |
| 2010/0128932 A1 | 5/2010 | Dvorkin et al. |
| 2010/0128933 A1 | 5/2010 | Derzhi et al. |
| 2010/0128982 A1 | 5/2010 | Dvorkin et al. |
| 2010/0131204 A1* | 5/2010 | Dvorkin ............... G06T 7/0004 702/6 |
| 2010/0135536 A1 | 6/2010 | Dvorkin et al. |
| 2011/0042079 A1* | 2/2011 | MacDougall ......... E21B 17/028 166/254.2 |
| 2011/0054796 A1 | 3/2011 | Ikeda et al. |

\* cited by examiner

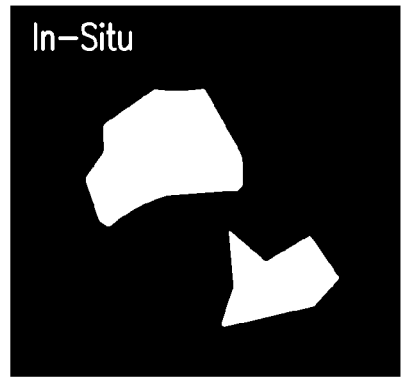 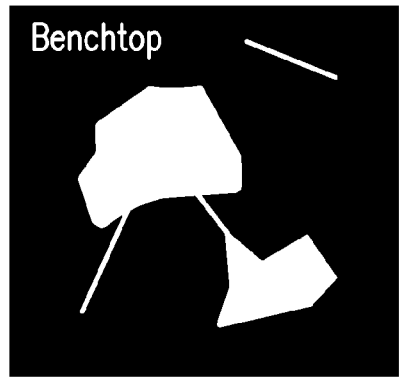
FIG. 11A        FIG. 11B
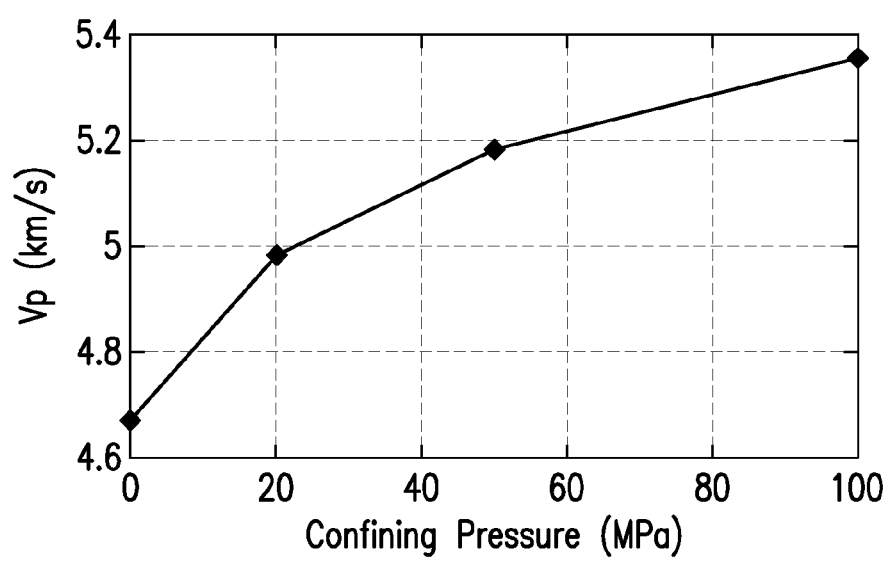
FIG. 12A

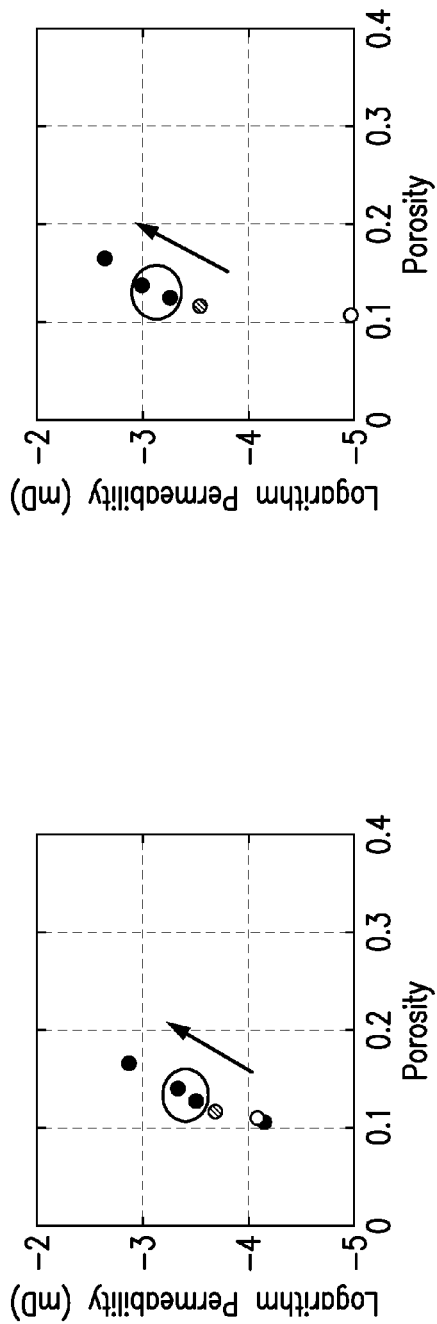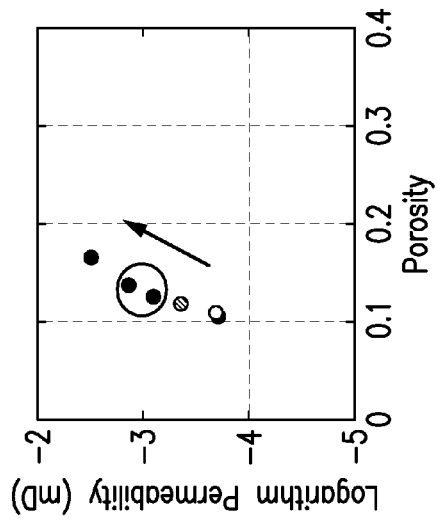

METHOD AND SYSTEM FOR INTEGRATING LOGGING TOOL DATA AND DIGITAL ROCK PHYSICS TO ESTIMATE ROCK FORMATION PROPERTIES

This application claims the benefit under 35 U.S.C. §119(e) of prior U.S. Provisional Patent Application No. 61/484,254, filed May 10, 2011, which is incorporated in its entirety by reference herein.

BACKGROUND OF THE INVENTION

The present invention relates to methods and systems for integrating logging tool data and digital rock physics to estimate rock formation properties. More particularly, the present invention relates to estimating rock formation properties with integration of logging tool data obtained from a subsurface rock formation and digital rock physics using digital computer tomographic (CT) and/or scanning electron microscope (SEM) images of rock samples retrieved from the same interval of the formation.

Exhaustive formation characterization from remote measurements that include seismic reflection profiling, well logging, and well testing requires a set of controlled laboratory experiments conducted on rock samples that represent the formation under examination. Even if the bulk density, elastic-wave velocity, and mineralogy are directly measured in the well, the permeability (especially relative permeability) and capillary pressure curves are not. Even if well tests are conducted, the permeability cannot be directly derived simply because the formation response to pressure and fluid flux variations that include, permeability, and a number of other quantities, such as porosity, fluid and formation compressibility, and reservoir geometry. These tests cannot replace controlled laboratory measurements where the absolute and relative permeability are measured on a set of samples covering ranges of porosity and mineralogy and at varying fluid content inside the pores space.

Typically, relations between the elastic properties and porosity and mineralogy are established in the laboratory, generalized by rock physics theory, and then applied to seismic data, which reflect the elastic properties of the subsurface, to infer the as yet unknown porosity in the remotely sensed formation. The same principle is true for permeability: a relation between permeability and porosity and lithology is established in the laboratory and then applied to appropriate well log curves (density, neutron porosity, NMR) to infer the permeability in the logged interval.

The problem is that in order to conduct controlled experiments in the physical laboratory to cover a relevant range of rock property variation, a fairly large set (>20) of well preserved and regularly shaped plugs at least an inch in length and diameter is required. Even if such plugs are available, conducting special core analysis (SCAL) for relative permeability and capillary pressure is extremely difficult and requires a long time, from weeks to months.

Methods and apparatus for subterranean formation flow imaging have been disclosed, e.g., in U.S. Pat. No. 6,856,132. There are four broad categories of estimation techniques which have been used in the oil and gas industries: logging tools, physical laboratory experiments, pressure transient tests/analysis, and digital rock physics. Logging tools and digital rock physics are described below.

Logging instruments, such as the Modular Formation Dynamics Tester manufactured by Schlumberger Oilfield Services, have been used to measure the formation and fluid properties in-situ. The temperature, pressure, composition, capillary tension, and viscosity of oil, gas and water and mixtures thereof are inputs to calculating relative permeability. In addition to fluid properties, it is necessary to know the petrophysical parameters of a geological formation such as fluid saturation, the porosity of the formation and its permeability. Formation porosity is the pore volume per unit volume of formation; it is the fraction of the total volume of a rock sample that is occupied by pores or voids. The saturation of a formation is the fraction of its pore volume that is occupied by the fluid of interest. Thus, water saturation is the fraction of the pore volume that contains water. The water saturation of the formation can vary from 100 percent to a small value that cannot be displaced by oil, and is referred to as the irreducible water saturation. In most cases it is assumed that the hydrocarbon saturation of the formation is equal to one minus the water saturation. Obviously, if the formation's pore space is completely filled with water, such a formation will not produce oil or gas and is of no interest. Conversely, if the formation is at an irreducible water saturation, it will produce all hydrocarbons and no water. Finally, the permeability of a formation is a measure of the ease with which fluids can flow through the formation, i.e., its producibility.

Traditional methods for measuring these producibility parameters involve wireline logging or logging while drilling (LWD) techniques that generally include resistivity, gamma, and neutron-density measurements, commonly known as the "triple-combo." For wireline measurement, a tool is lowered below the zone of interest on an armored multiconductor cable that provides power and communications. The tool is then moved up and down through the borehole making measurements along the way. In the instance of LWD, the measurements are made while drilling is taking place. In this case the tool is mounted on specialized fixtures in the drilling string. Each of these methods has advantages and disadvantages. The wireline method is generally capable of providing a more accurate measurement than LWD, and the data is acquired in real time. The LWD method is susceptible to effects such as tool position within the borehole and making the measurements in a relatively new borehole prior to drilling fluids entering the formation. The triple combo measurements are subject to a number of effects from the borehole environment. Resistivity tools respond to conductive fluids, including moveable water, clay bound water, capillary bound water and irreducible water. A number of models have been developed to estimate the water saturation of a formation. However, the recognition of pay zones within a rock formation is difficult because the conductivity difference between capillary-bound water and displaceable water cannot be measured. In addition, resistivity measurements are subject to borehole rugosity and mudcake effects. Similarly, neutron-density measurements respond to all components within the formation but are more sensitive to the formation matrix as opposed to the fluids contained therein. Even after cross plot corrections, borehole rugosity, mudcake, lithology and other environmental effects can adversely effect the measurement.

Nuclear magnetic resonance (NMR) logging is a relatively recent commercial method employed in wireline logging to estimate formation parameters and other parameters of interest, for a geological formation. Unlike nuclear porosity logs, which utilize isotopic radioactive sources, the NMR measurement is environmentally safe and is less affected by variations in matrix lithology than most other logging tools. NMR logging is based on an assembly of magnetic moments, each having a certain angular momentum. When exposed to a static magnetic field they tend to align at a certain angle to the direction of the magnetic field, and will process with the Larmor frequency around the direction of the magnetic field. The rate at which equilibrium is established upon provision of a static magnetic field is characterized by the parameter $T_1$, known as the spin-lattice relaxation time. Another related NMR parameter is the spin-spin relaxation time constant $T_2$ (also known as transverse relaxation time) which is an expression of the relaxation due to dynamic non-homogeneities on molecular length scales.

The MRIL® tool manufactured and utilized by the NUMAR product service line of Halliburton Energy Services and the CMR™ tool manufactured and utilized by Schlumberger Oilfield Services represent recent developments in the field of NMR logging and are both suitable for inferring porosity, permeability, and fluid type.

Using $T_1$ and/or $T_2$ relaxation times, one can determine a number of formation properties. Porosity can be estimated by means of signal intensity. Fluid typing utilizes $T_1$, $T_2$ and/or diffusion measurements and is usually based on the geometry and sizes of the pores, as well as by the viscosity of the fluid being measured. The bulk volume index (BVI) and free fluid index (FFI) are measured based on $T_2$ and empirically derived formulas. The formation permeability estimates are based on $T_1$ and/or $T_2$ measurements and one of several empirically derived models.

With respect to permeability, several models have been used to estimate formation permeability. The first method is based on $T_1$ and/or $T_2$, porosity and is estimated by various oilfield service and oil exploration companies according to equations 1-3 below:

$$k \approx \phi^4 T_1^2 \qquad [1]$$

$$k = C\phi^4 T_{2ML}^2 \qquad [2]$$

$$k \approx \phi^2 T_1^2 \qquad [3]$$

where k is permeability, $\phi$ is porosity, C is an empirically derived constant and $T_{2ML}$ is the logarithmic mean of the $T_2$ distribution.

Yet another model estimates formation permeability based on the bound water information (often referred to as the Coates model) according to equation 4 below:

$$k \approx \left[\left(\frac{\phi}{C}\right)^2 \left(\frac{FFI}{BVI}\right)\right]^2 \qquad [4]$$

where FFI is the free fluid index, which is determined by partitioning the total measured NMR response by the $T_{2cutoff}$, which is the value of $T_2$ that is empirically related to the capillary properties of the wetting fluid for the specific formation lithology. The porosity estimate below $T_{2cutoff}$ is generally referred to as the bound fluid porosity or bulk volume irreducible (BVI). While estimates of $T_{2cutoff}$ values have been made for various types of mineralogy, the only accurate means of determining $T_{2cutoff}$ is by performing NMR measurements on a core sample.

Another model for estimating formation permeability is based on the restricted diffusion and pore size of the formation as set forth in equation 5 below:

$$k \approx \phi^3/((1-\phi)^2 \tau (S/V)^2) \qquad [5]$$

where S/V is the pore surface to volume ratio and $\tau$ is the rock tortuosity.

Each of the above models has drawbacks in their application. For instance, equation 4 (the Coates model) may not be valid if gas is present in the sample or if the estimate of the $T_{2cutoff}$ is significantly in error. The Kozeny-Carman model set forth in equation 5 was derived for an artificial pore-space geometry (parallel pipes) and has to be adjusted over wide range of reservoir lithology, including such parameters as grain size distribution and pore shape.

Other logging techniques have been used to estimate formation permeability. Primary among them is the use of formation test tools to determine formation permeability. A formation test tool is lowered into the borehole and brought into contact with the formation wall. A probe is inserted past the mud cake to come in contact with the formation itself. Fluid is then withdrawn from the formation using a precharge piston or pumping means. This "pressure draw down" period induces fluid into the tool that may be diverted to sampling chambers or, ultimately, discharged back into the borehole. Following the pressure draw down, formation pressure can be measured as the pressure returns to the natural formation pressure. There are a number of models for estimating permeability based on the formation pressure and temperature tool data. These models may include a laminar or spherical model design. The use of formation testers to determine permeability is known, and U.S. Pat. Nos. 6,047,239, 5,247,830, and 4,745,802, for example, set forth exemplary formation test tools. As noted previously, these formation test evaluation techniques pre-suppose the use of a particular model, which in turn pre-supposes the nature of the formation itself. The formation may be thinly laminated near the test point or have a large, consistent lithology. It is well known that models designed to work in a consistent lithology will not yield an accurate result where the formation is thinly laminated with the layers each having differing porosity and permeability characteristics. Formation test tools are generally incapable of measuring anisotropic permeability, i.e., vertical versus horizontal permeability. An additional downside to using formation test tools is the fact that logging tool movement must be stopped to permit the formation test tool to come into contact with the formation, perform the draw down and permit the pressure to build back up. It may require several minutes to hours to perform the draw down and build up. In this case, prior to wireline logging operations, the drill string must be "tripped" or removed from the borehole to permit logging. This results in costs in addition to the cost of services associated with logging. The "triple combo test" and NMR logging tools noted above are used in continuous logging operations, that is, the measurements are made as the tool is moved up or down the borehole at rates exceeding three feet per minute. Modern borehole logging speeds typically exceed 30 feet per minute. Thus, while providing some information regarding permeability, formation test tools are costly to use when compared to NMR logging tools. At the same time, NMR logging tools make certain assumptions regarding permeability that may not be accurate in light of actual formation conditions.

Recently, some efforts have been made to combine NMR techniques with formation test tools. Halliburton, Schlumberger and Baker Atlas have introduced techniques in which fluid identification is performed on the fluid withdrawn from the formation during one of the formation tests. Examples on these types of techniques are set forth in U.S. Pat. Nos. 6,111,408 and 6,111,409. In each instance, the NMR experiment is performed on the fluid that is no longer in situ. As a result, the fluid may undergo a phase change when removed from the downhole environment.

Downhole Fluid Analysis (DFA) typically is necessary to calculate formation properties such as absolute permeability, relative permeability, and capillary pressure. Typical logging techniques extract a sample from the well bore and transport it to the surface for analysis. Tests used to quantify fluid composition are typically chromatographic methods. These lab tests are subject to error due to transport and changes of the material properties that may occur in replicating downhole conditions. In addition, it is well known that the fluid in a well or formation is not homogeneous and the fluid properties vary in both time and depth location. Logging tool samples are small and represent a very small percentage of the overall fluid in the well. Multiple samples can be taken but this requires significant time and expense. Recently, some companies such as Schlumberger, have developed in-situ analysis techniques based on spectroscopy. Schlumberger's MDT family of tests includes In-Situ Family (density, composition, gas-oil ratio, $CO_2$, pH, fluorescence, color and fluid profile), Composition Fluid Analyzer ($C_1$, $C_2$-$C_5$, $C_6$+, $H_2O$, $CO_2$), Live Fluid Analyzer (analyzes fluids as they flow through the MDT), MDT Permeability ($k_v$ and $k_h$ estimates are usually based on 1000 $cm^3$ samples of reservoir fluid), MDT Single Phase (PVT-quality single-phase fluid sample removed from the reservoir), MDT Low Shock Sampling (limits pressure drawdown during fluid sampling), and Combinable Magnetic Resonance (estimate the distribution of pore sizes in the formation and identify hydrocarbons in low-contrast, low-resistivity pay zones with high-resolution NMR). The availability of in-situ fluid composition techniques has made it possible to estimate formation properties such as relative permeability. The estimation of relative permeability in this manner is indirect. The detailed structure of the formation pore structure typically is not determined and known by sensing done with a conventional logging tool. Many factors such as contamination of fluids with drilling mud and non-representative sample locations can introduce significant errors in the logging tool estimates of relative permeability. These errors are magnified in tight formations such as carbonates and shale or tight-gas sandstone.

The other broad technique for formation analysis, digital rock physics, utilizes rock samples withdrawn from the formation and evaluated in the computational rock physics laboratory. The rock sample may be from a core sample, drill cuttings or other suitable means. Samples are selected to be as representative of the formation as possible. CT scan imaging of a sample of rock formation is used to produce a numerical object that represents the material sample digitally in the computer. The raw CT scan data is further processed or segmented to produce an accurate 3D digital representation of the selected sample. Subsequent numerical simulations of various physical processes include viscous fluid flow (for permeability estimation); two phase fluid flow (for relative permeability estimation); stress loading (for the effective elastic moduli); electrical current flow (for resistivity); and pore size distribution for nuclear magnetic resonance relaxation time properties, including distributions of the relaxation time.

A rock sample is placed inside a CT-scan machine where it is illuminated with focused X-rays of desired frequency. This frequency determines the resolution of the image—the size of a single voxel can vary from a few nanometers to a micron and to a centimeter. The sample is mechanically rotated inside the machine to view it at all angles. The software supplied with the machine tomographically reconstructs the 3D volume. These images come in shades of gray. The gray level is directly affected by the average atomic number of the material, which is, simply speaking, its average density. For example, if the rock fragment under examination contains dolomite, calcite, quartz, porous clay, and air in the large pores, the brightness of the voxels representing these entities will reduce from almost white for dolomite to almost black for the pores. The porous clay will appear as a darker gray because (depending on its intrinsic porosity) its bulk density is smaller than that of the pure clay mineral. This method may not necessarily resolve the individual clay particles, but it will identify the clay and can estimate its porosity by assuming the density of the clay mineral that is related to the clay type. The same holds for porous micrite in carbonates. If the pores contain fluids with a significant density contrast (e.g., water and air), the fluid phases can be identified in the CT image.

A nano-CT machine can resolve small micritic grains. It can also resolve relatively large shale particles but not the smallest clay platelets. To image the latter, FIB-SEM (focused ion beam combined with scanning electronic microscope) technique is commonly used. The ion beam removes the rock material above the cutting plane and exposes a flat unaltered area, which is then imaged by SEM. Such 2D images can be obtained sequentially at extremely close planes. Then these 3D images are combined to produce a tomographic 3D image at a very high (5-10 nm) resolution. The entire gray-scale range of the image can be reduced to a few integers, such as 0s for pores, 1s for quartz, and 2s for calcite. This procedure is based on fairly sophisticated image-processing algorithms (rather than simple intensity/color thresholding) and is essential for any process simulation as it strictly defines the pore space where the fluid flows and the mineral phases through which the elastic stress is transmitted. FIGS. 1A, 1B, and 1C display a segmented image, 0s (black) for the pores and 1s (gray) for calcite with the same sample displayed with increasing magnification from left to right in these figures. The smaller features of the pore space become apparent as magnification increases. After a digital image is acquired and segmented, fluid flow can be simulated in the digital pore space and relative permeability curves are computed, such as illustrated in FIGS. 2A-2B (black dots=gas, grey dots=water). In FIGS. 2A and 2B, relative permeability curves for water and gas in the same sandstone sample are shown, with varying interfacial tension (from left to right in these figures). A salient feature of such calculations is that the pore space and mineral matrix of the segmented image are not replaced by an idealized geometry (as in, e.g., network modeling). Rather, the image is used directly, with all its visible intrinsic complexity intact.

In characterizing formation characteristics, absolute permeability $k_{Absolute}$ is often defined from Darcy's equation $$Q = -k_{Absolute}\left[\frac{A}{\mu}\frac{dP}{dx}\right] \qquad [6]$$

where Q is the volume flux through the sample ($m^3/s$); A is the cross-sectional area of the sample ($m^2$); $\mu$ is the dynamic viscosity of the fluid (Pa·s with 1 cPs=10-3 Pa·s); and dP/dx is the pressure drop across the sample divided by the length of the sample (Pa/m). Theoretically, the absolute permeability depends only on the pore-space geometry but not on the pore fluid. A simple and powerful equation to estimate $k_{Absolute}$ is the Mavko-Nur (1997) modification of the Kozeny-Carman equation:

$$k_{Absolute} = \frac{d_{Mean}^2}{72\tau^2} \frac{(\phi - \phi_p)^3}{[1 - (\phi - \phi_p)]^2} \quad [7]$$

where $d_{Mean}$ is the mean grain size; $\tau$ is the tortuosity; $\phi$ is the total porosity; and $\phi_p$ is the percolation porosity (porosity at which the pore space becomes disconnected and, hence, permeability becomes zero). Permeability has the same units as $d^2_{Mean}$.

Timur introduced one of the most commonly used equations that link the absolute permeability to porosity $\phi$ and irreducible water saturation $S_{wi}$:

$$k_{Absolute} = 8581\phi^{4.4}/s^2_{wi} \quad [8]$$

where $S_{wi}$ are in unitless volume fractions and $k_{Absolute}$ is in mD. Equation 8 is used to calculate the irreducible water saturation from the permeability (in mD).

All of these equations have been verified by and calibrated to a finite number of datasets which are often idealized or artificial (e.g., the Fontainebleau sandstone or glass beads). To become applicable to the variety of formations encountered in real-world petroleum exploration, these equations have to be re-adjusted for each single formations type and these readjustments cannot be known a-priori.

Absolute permeability varies with porosity and Rothman and Zaleski (Rothman, D. and Zaleski, S., *Lattice-Gas Cellular Automata*. Cambridge, UK: Cambridge University Press, 1997. Pages 155-157) have studied this variation within a rock sample. They scanned and segmented a 2 mm×2 mm rock sample of Fontainebleau sandstone and computed porosity and absolute permeability at several scales covering sizes of 56, 112 and 224 voxels (voxel size of 7.5 μm). They found that porosity varied over a factor of four for the smallest to largest samples with corresponding variation in absolute permeability.

Relative permeability is used to quantify multiphase flow, such as the flow of oil in the presence of water and water in the presence of oil. In a sample with two such fluids, the relative permeabilities $k_{ro}$ and $k_{rw}$, by definition, are $$k_{ro} = -\frac{Q_o \mu_o}{k_{Absolute} A d p/dx}, \quad [9]$$

$$k_{rw} = -\frac{Q_w \mu_w}{k_{Absolute} A d p/dx} \quad [10]$$

where the subscripts "o" and "w" refer to oil and water, respectively. The fluxes $Q_o$ and $Q_w$ are measured at fixed water saturation $S_w$. Relative permeability is usually plotted versus Sw. Because these fluxes of the fluid phases at partial saturation are smaller than the flux measured in a sample fully saturated with water or oil, the relative permeability is always smaller than 1 and larger than or equal to 0. Typical $k_{ro}$ and $k_{rw}$ versus $S_w$ curves produced by digital two-phase flow simulations are displayed in FIG. 3.

The relative permeability depends on more factors than $k_{Absolute}$, including the wettability of the fluids and minerals system, interfacial surface tension, and viscosity contrast between the fluid phases. These parameters may vary in space and time, the latter due to pressure, flow, and the resulting hydrocarbon state and composition changes during production.

To estimate permeability for single as well as two-phase fluid flow, the lattice-Boltzmann computational method (LBM) can be used to solve the Navier-Stokes Equations. LBM is based on Newtonian dynamics of particles traveling and colliding on a 3D spatial grid. With the collision rules appropriately specified, the particle speed and pressure fields precisely mimic those governed by the Navier-Stokes equations for viscous flow. The importance of LBM for fluid-flow simulation is that the no-slip boundary conditions can be implemented at the fluid-solid boundaries of any geometry (as imaged), which is essential in real pore space. For a multiphase flow, the wettability angles, interfacial tension, and viscosities are specified prior to computation. The elastic properties are simulated using a finite-element method (FEM) with the elements placed in the mineral matrix and their elastic moduli assigned according to the mineral types as determined during segmentation. This is not a purely mathematical procedure as it requires a decision by a geologist and petrophysicist to select minerals appropriate to the rock under examination. Sometimes selected SEM images are taken to better understand and identify the rock.

The electrical conductivity is also computed using SEM with the elements placed in the pore space and conductive minerals. Similar to other simulations, the conductivities of the individual phases are specified prior to calculations.

Because these computational experiments are conducted on the same digital object and in precisely imaged pore space, the named attributes of rock can be interrelated.

Some advantages of logging techniques per se can include, for example, the following.

1. The ability to directly sample formation fluids at in-situ conditions and calculate their chemical composition and mechanical properties.

2. Logging techniques combined with well tests also provide a series of well tests that estimate reservoir flow properties at the near-wellbore as well as in the far field. These property estimates can be provided in the horizontal and vertical directions thus estimating flow-property anisotropy.

3. Log data of GR, density, neutron porosity, and NMR can be used to estimate the mineralogy, porosity, and the pore-size distribution.

Some disadvantages of logging techniques per se can include, for example, the following.

1. Flow properties provided do not directly calculate permeability. Rather these direct measurements reveal the diffusivity, a combination of permeability, porosity, fluid compressibility, and matrix compressibility. The assumed reservoir geometry is also a key input into inferring permeability from well tests. As a result, the estimates of permeability and relative permeability are subject to significant error and variability. These errors may differ significantly depending upon the type of rock formation being evaluated.

2. The flow properties provided by logging tools are snap-shots in time and space. As such they lack forecasting power to predict how the reservoir behaves at different stages of development as fluid saturations and fluid properties change versus pressure and temperature.

3. Mineralogy, porosity, and the pore-size distributions from logging tools are indirect measurements. They are interpretations of the responses of the formation to different excitations and are therefore only indirectly related to the parameters of direct interest.

4. Fluid samples taken by logging tools are small and may not represent the fluid properties of the entire formation. Fluid properties are not the same at all locations within a formation.

5. Fluid samples taken with logging tools may be contaminated with drilling fluid when the samples are taken on a newly drilled well.

6. Fluid samples taken by logging tools depend upon a seal of the sampling tool at the surface of the well bore. The irregularity of the surface at the well bore can interfere with this seal. In addition, tight formations such as carbonates or shales require high pressures to inject or withdraw formation fluid samples. In these cases a tight seal is very difficult to achieve.

Some advantages of digital rock physics techniques per se can include, for example, the following.

1. A mathematical model of the intimate texture of rock (e.g., whether it is cemented or loose) as well as the position of various minerals relative to the pores space (e.g., grain-coating kaolinite of pore-obstructing illite, etc) provide a very accurate representation of rock structure.

2. Direct simulation of processes inside the digital sample can deliver all rock properties from the same rock object.

3. Digital rock physics provides the ability to vary at will the conditions of the computational experiment thus covering rock response at any foreseeable conditions during the life of the reservoir, including depletion, injection, as well as thermal treatment.

4. From very small fragments of rock, digital rock physics can deduce relations between pairs of rock properties, such as permeability versus porosity, formation factor versus porosity, elastic properties versus porosity, and so forth.

Some disadvantages of digital rock physics per se can include, for example, the following.

1. Samples typically range in size from a few millimeters to a few centimeters in size. Such samples may not be perceived as representative of the entire well or formation.

2. The digital images of rock samples are derived from samples scanned at the surface of the earth. Methods have been developed to correlate rock properties at earth surface conditions with rock properties at in-situ conditions. Reliance on such correlations is perceived as risky or error prone by some well operators.

3. In order to compute rock properties such as relative permeability and capillary pressure that are dependant on rock and fluid conditions, digital rock physics must make estimates of the fluid densities, wettability, and viscosities to be used in computations. There is no way to concretely verify these estimates.

The present investigators have recognized a need in the industry for integration of well logging and digital rock physics technologies to yield unique rock formation evaluation capabilities and enhanced formation models.

SUMMARY OF THE INVENTION

A feature of the present invention is obtaining a rock sample from a logging tool such as a sidewall plug or large enough cutting extracted by the logging tool in the same well interval that the logging tool measures fluid properties. The rock samples thus obtained are scanned using a computer tomographic (CT) scanner, scanning electron microscope (SEM), or other suitable scanning device. The resulting scanned rock image is segmented and rock properties comprising porosity, absolute permeability, relative permeability, capillary pressure, and/or other relevant rock properties are calculated. The integration of enhanced digital rock physics techniques with downhole well logging according to the present invention can correct and/or support upscaling of the well logging results relative to the rock formation of interest.

To achieve these and other advantages and in accordance with the purposes of the present invention, as embodied and broadly described herein, the present invention relates to using porosity, absolute permeability, relative permeability, and/or capillary pressure curves computed from digital rock physics along with the in-situ temperature, pressure, composition and viscosity of the mixtures of oil, gas, and water, NMR data, and/or estimates of relative permeability from logging tools, to generate absolute permeability versus porosity trends at in-situ conditions that are used to expand the datum obtained from logging tools into a permeability-porosity transform accounting for the natural porosity variations within the reservoir sampled by the logging tool.

Porosity, absolute permeability, relative permeability, and/or capillary pressure curves computed from digital rock physics along with the in-situ temperature, pressure, composition, and viscosity of the mixtures of oil, gas, and water, NMR data, and estimates of relative permeability from logging tools can be used to generate elastic properties versus porosity and mineralogy with in-situ fluids present in the pores and for a range of in-situ fluid saturations.

Porosity, absolute permeability, relative permeability, and/or capillary pressure curves computed from digital rock physics along with the in-situ temperature, pressure, composition, and viscosity of the mixtures of oil, gas, and water, NMR data, and estimates of relative permeability from logging tools can be used to generate an electrical formation factor and the m and n Archie's constants properties versus porosity and mineralogy with in-situ fluids present in the pores and for a range of in-situ fluid saturations.

Porosity, absolute permeability, relative permeability, and/or capillary pressure curves computed from digital rock physics along with the in-situ temperature, pressure, composition, and viscosity of the mixtures of oil, gas, and water, NMR data, and estimates of relative permeability from logging tools can be used to generate relative permeability versus porosity curves for the in-situ fluid properties varying in ranges plausible to encounter during the life-time conditions of the reservoir.

Porosity, absolute permeability, relative permeability, and/or capillary pressure curves computed from digital rock physics along with the in-situ temperature, pressure, composition, and viscosity of the mixtures of oil, gas and water, NMR data, and estimates of relative permeability from logging tools can be used to generate wettability versus porosity curves for the in-situ fluid properties varying in ranges plausible to encounter during the life-time conditions of the reservoir.

Porosity, absolute permeability, relative permeability, and/or capillary pressure curves computed from digital rock physics along with the in-situ temperature, pressure, composition, and viscosity of the mixtures of oil, gas and water, NMR data, and estimates of relative permeability from logging tools can be used to generate capillary pressure versus saturation and porosity curves for the in-situ fluid properties varying in ranges plausible to encounter during the life-time conditions of the reservoir.

Porosity, absolute permeability, relative permeability, and/or capillary pressure curves computed from digital rock physics along with the in-situ temperature, pressure, composition and viscosity of the mixtures of oil, gas and water, NMR data and estimates of relative permeability from logging tools can be used to create a database of digital rock physics trends for various formation types and to correlate these with measurements from logging tools such that corrections can be made to estimates from logging tools for the complexity of actual rock pore structures.

A further feature of the present invention is verification and calibration of logging tool estimates of rock properties by contrasting them to the properties computed on rock samples using digital rock physics extracted.

A further feature of the present invention is use of digital rock physics to enrich logging tool results by providing insights into the pore-scale rock structure.

A further feature of the present invention is use of a digital rock sample analogue in lieu of or in conjunction with an extracted rock sample and in-situ the fluid properties produced by the logging tool to compute improved rock properties.

While the inventors have found that trends produced as described in the present invention can represent the range of rock properties in a facies, well, or formation, it remains important to select those rock properties which are most representative of the facies, well, or formation. The present invention also includes a method to select one or more digital sub-samples that are most representative of the facies, well or formation.

A further feature of the present invention is digital simulation of logging tool transient pressure tests by using the digital rock structure obtained from scanning and segmentation of the rock sample extracted by the logging tool and the downhole fluid properties from the logging tool. The simulated transient pressure response and the actual pressure response are correlated to make corrections to the porosity, permeability and relative permeability estimated by the logging tool.

BRIEF DESCRIPTION OF DRAWINGS

FIGS. 11A-B are magnified sectional views of thin cracks which appear in a solid matrix of rock sample due to stress reduction from in-situ to benchtop conditions.

FIGS. 12A-C show plots of P-wave velocity (top) and permeability (middle) versus confining stress in tight gas sandstone of about 0.05 porosity. Permeability is plotted versus velocity in the FIG. 12C.

FIGS. 20A-C are similar plots as FIGS. 16A-C but for all six digital samples displayed in FIG. 14. The arrow shows the direction of increasing crack porosity. The data points within the in-situ permeability range are encircled in blue.

DETAILED DESCRIPTION OF THE PRESENT INVENTION

Figure 1A:
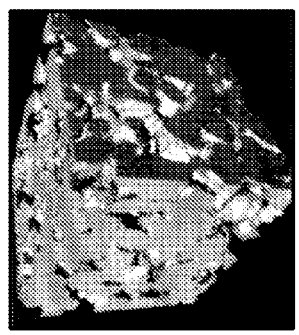
FIGS. 1A-1C show a segmented image for calcite, with 0s (black) for the pores and 1s (gray) for the calcite solids. The images of FIGS. 1A-1C are (left to right) about 20, 8, and 2 microns across.

The present invention relates in part to integrating logging tool data and digital rock physics in unique ways to estimate rock formation properties more accurately. The present methods can at least partly resolve or remedy shortcomings of either a logging tool or digital rock physic evaluation strategy if used alone. The present methods and systems, for example, can reduce or eliminate needs for conducting time-consuming laboratory analyses outside the well to analyze properties of a rock sample for use in estimating permeability, porosity, or other rock properties, while taking advantage of real time in-situ fluid and well property measurement capabilities of a logging tool. The present invention further relates in part to estimating rock formation properties with integration of logging tool data obtained from a subsurface rock formation and digital rock physics using digital computer tomographic (CT) and/or scanning electron microscope (SEM) images of rock samples retrieved from the same interval of the formation. For purposes of the detailed description herein, references to "CT scanning" and similar wording alone as used for convenience, may alternatively or additionally encompass SEM scanning unless indicated otherwise.

In a method for making estimates of subterranean rock properties, for example, a logging tool is positioned inside a well bore, wherein in situ fluid and/or well properties in the well are measured using the logging tool. These measurements can be made in a single well interval in the well, or multiple intervals of interest in the well. For purposes herein, "well interval" refers to a well location, such as a depth range in the well or formation in which the well is drilled. Rock properties in the well can be estimated for a location of the logging tool using the measured in situ well properties. At least one rock sample is retrieved from the well. The retrieved rock sample or samples are prepared for digital rock physics analysis, and then scanned to produce a digital image of the rock sample. The digital image of the rock sample is segmented to define pores and grains in the digital image, and then the digital image is adjusted to represent the rock properties at in-situ conditions using the well properties. Rock properties are calculated from the adjusted digital image of the rock sample using the in situ fluid properties. The rock properties in the well derived from the logging tool measurements are compared with the rock properties derived from the digital image of the rock sample or samples using the in situ fluid properties. The in-situ fluid properties used in this method can be, for example, temperature, pressure, viscosity, and/or chemical composition, or any combinations thereof. The in-situ well properties used in this method can be, for example, downhole images, well bore gauge, temperature, pressure, resistivity, gamma, neutron-density, and/or $T_1$ and $T_2$ relaxation times from NMR, or any combinations thereof. The rock properties calculated and compared in this method can be, for example, absolute permeability, total porosity, connected porosity, relative permeability, capillary pressure, m and n Archies constants, elastic moduli, and/or electrical properties, or any combinations thereof.

In a method of the present invention, referred to as "the Point Method," the process comprises the use of a logging tool, such as Schlumberger's Modular Formation Dynamics Testing Tool (MDT) capable of downhole images, gauge hole information, temperature, pressure, fluid composition, pressure transient test, triple combo test, $T_1$ and $T_2$ relaxation times from NMR, and/or other available data. A traditional logging tool can be modified to include a micro-sidewall coring device. Traditional sidewall cores can range in size from several cm down to a few mm in size. Small core samples, for example, of about 2 mm diameter by about 2 mm in length or smaller can be produced from the micro-sidewall sampling tool used in the present methods. The size of the core sample can be selected to be suitable for subsequent CT scanning and digital rock physics analysis. There can be an unexpected benefit from the small core sample size. In brittle formations such as quartz and carbonate dominated shale or tight-gas sandstone, coring tools and percussive tools can fracture the rock making a large traditional sample difficult or impossible to acquire. The very small size required for digital rock physics makes it possible to produce usable samples even in brittle formations. In addition, tight formations such as shale are difficult to drill and may be impervious to percussion sampling. Smaller sample sizes specified in the present invention make sampling possible in formations that otherwise would be difficult or impossible to sample. The core sample cutting device could be percussion, rotary core, or other techniques capable of producing a core sample. The depth of the core sample is sufficiently deep to go beyond any expected heating from the BHA of the drill strings, typically about one half inch or more for most cases. The logging tool data can be combined and analyzed to select an exact depth and azimuth for the micro-sample retrieval tool. The depth selection can be made to avoid irregular features in the formation such as fossils, burrows, shale stringers in carbonates or sandstones, micro-fractures, and/or any other non-representative features. The micro-samples are taken over the same well interval or intervals as the logging tool. In this interval, the micro-samples can be taken before, during, and/or after the logging tool has finished its analysis and the micro-sidewall coring device cuts a sample. The micro-sample thus retrieved, combined with the downhole images, gauge hole information, temperature, pressure, fluid composition, pressure transient test, triple combo test, $T_1$ and $T_2$ relaxation times from NMR, and/or other available data, can then be analyzed using digital rock physics techniques to calculate $k_{absolute}$, total porosity, connected porosity, $K_r$, $P_c$, m and n Archie's constant properties, elastic moduli, and/or electric properties, and/or other properties for a given lithofacies. This saves time and cost compared to producing a full core, doing a full core CT scan and segmentation, selecting the representative plugs for analysis, selecting micro-samples to verify representative analysis, and then doing complete digital rock physics calculations. The combination of logging tool data and digital rock physics calculations done in the manner of the present invention have the following advantages.

1. The digital rock physics calculations are more representative because the location of the rock sample selected for analysis is accurately matched with the location of the downhole fluid analysis.

2. Calculation of relative permeability is improved when compared to the estimates traditionally made by logging tools because the calculations are direct (e.g., based on the scan of an actual rock sample) and not indirect (e.g., such as estimated from pressure transient and other test data).

3. Errors in porosity, permeability, relative permeability and other rock properties estimated from logging tools increase as porosity decreases, tortuosity increases and pore structure complexity increases. This is because the correlation of downhole tests such as pressure transient test, NMR, and other tests with actual rock properties decreases as the rock structure becomes more complex and less ideal. The combined logging tool and digital rock physics methods of the present invention overcome these deficiencies for directly computing rock properties in complex formations such as shales, carbonates, and tight gas sandstone.

In another method of the present invention, referred to herein as "the Trend Method," the process comprises the use of a logging tool, such as Schlumberger's Modular Formation Dynamics Testing Tool (MDT), capable of downhole images, gauge hole information, temperature, pressure, fluid composition, pressure transient test, triple combo test, $T_1$ and $T_2$ relaxation times from NMR and/or other available data in combination with the digital rock physics analysis as described in the Point Method above. Several digital samples of the segmented rock sample can be retrieved by the logging tool and numerically divided into a number of sub-cubes. Eight sub-cubes (2×2×2) or more (e.g., 3×3×3) may be used for example. Plotting pairs of selected rock properties, elastic moduli versus porosity for example, produces a trend. Such computationally-derived trends comply with those produced in the physical laboratory on similar rock material and/or with the trends predicted by relevant theoretical models. Elastic wave properties in rock versus porosity is one theoretical model which can be used for this purpose. The relationship between elastic wave velocity and porosity can be theoretically predicted in the absence of cracks in the rock to produce a trend. When the calculated absolute permeability for a sub-sample falls on the same trend line as predicted from the elastic wave velocity versus porosity trend, the calculated absolute permeability can be used as a data point to form a permeability versus porosity trend because the selected sub-sample does not contain cracks which would affect the absolute permeability calculation. Such a sub-sample is representative of the rock at in situ conditions. As referenced above, Rothman and Zaleski have also studied the variation of properties such as porosity and absolute permeability within a rock sample but their interpretation is limited to property variation within the rock sample. An unexpected benefit of the trends of the present invention is that they can be used in the field to estimate formation properties. This is unexpected because common wisdom would suggest that in order to assess that variation in rock properties one must take more rock samples from various locations within the well or formation. However, with the present invention, the variation within a lithofacies can be estimated from sub-sampling and extrapolating the trends produced from the sub-samples consistent with the expected or theoretical trend. In this way the number of required samples to estimate variation of rock properties within a given lithofacies is limited to the number of lithofacies present in the formation. This results in significant reduction in time and cost required to effectively estimate rock and formation properties. The inventors have found that the concept of trend is applicable not only for absolute permeability but also for the elastic and electrical properties of rock. The present invention also comprises the concept of verifying these trends by theoretical rock physics and upscaling these trends to the core and reservoir scale. Because the rock sample and fluid analysis used in these trend calculations were selected from approximately the same location within the formation, the resulting trend curve can be used to validate and/or correct subsequent estimates made by the logging tool. Moreover, the trend curves generated can be used over a wide range of fluid properties and fluid saturations to provide rapid and accurate estimates of well properties and producibility.

The present invention also comprises the Trend Method as described above where the parameters in the trend are permeability versus porosity accounting for the natural porosity variations in the formation.

The present invention also comprises the Trend Method as described above where the parameters in the trend are elastic properties versus porosity and mineralogy with in-situ fluids present in the pores and covering a wide range of fluid saturations.

The present invention also comprises the Trend Method as described above where the parameters in the trend are electrical formation factor and the m and n Archie's constants properties versus porosity and mineralogy with in-situ fluids present in the pores and covering a wide range of fluid saturations.

The present invention also comprises the Trend Method as described above where the parameters in the trend are relative permeability versus water saturation, wettability, and/or capillary pressure. Ranges for water saturation, wettability, and/or capillary pressure can be selected to cover plausible ranges encountered during the lifetime conditions in the reservoir.

Figure 4:
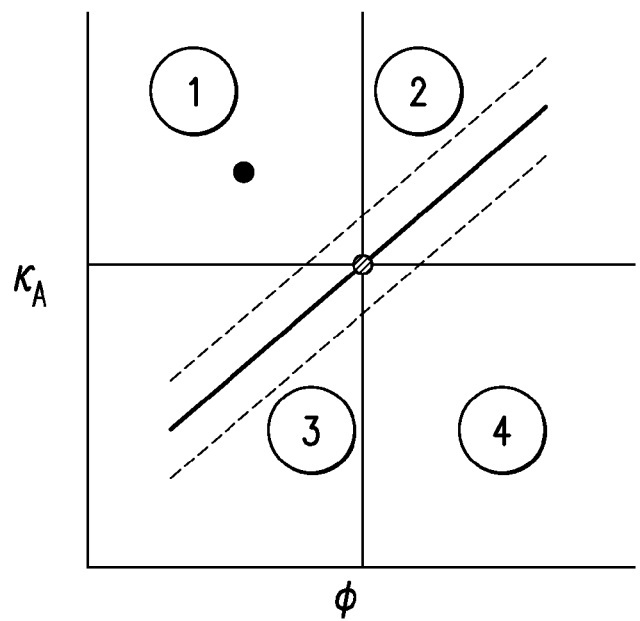
FIG. 4 shows a plot of a quadrant analysis of calculations produced by digital rock physics and a logging tool used in a method to upscale rock property results obtained from subsampling a small rock sample to estimate properties for subterranean facies or an entire formation according to the present invention.

The present invention also comprises building a database of results from the Trend Method as described above for a wide range of formation types including, but not limited to, sedimentary rocks such as siliciclastic rocks (sandstones and shales) and carbonates, igneous rocks, and metamorphic rocks. In addition, Trend Method data is gathered for a range of synthetically manufactured porous structures comprising sintered glass beads. The glass bead formations are highly regular and are completely open pore structures and as such can be considered "ideal" formations. Logging tool tests that indirectly measure permeability and relative permeability would correlate very well with an "ideal" structure such as sintered glass beads. In the case of an "ideal" formation an estimate of a rock parameter, such as permeability from a logging tool, would fall very close to the same rock property relationship produced by the Trend Method. Real world formations can be highly "non-ideal". Logging tool estimates of permeability, relative permeability, and other rock properties for such "non-ideal" formations will deviate from the property relationships produced by the Trend Method. A quadrant analysis of calculations produced by digital rock physics and a logging tool is shown in FIG. 4. This figure shows a typical trend generated by sub-sampling a given rock sample and performing the Trend Method analysis. The centrally-located dot in FIG. 4, which is the lighter (grey) dot located where the quadrant lines intersect as cross-hairs, is the absolute permeability and porosity obtained from digital rock physics for the micro-sample extracted from the formation using the logging tool. The dotted lines in FIG. 4 represent +/− three sigma variation for the digital rock physics analysis performed on the same rock sample. Using the digital rock physics data point (i.e., the centrally-located lighter (grey) dot) as the center of the plots, the graph space is divided into four quadrants labeled 1, 2, 3 and 4. The darker (black) dot located in quadrant 1 in FIG. 4 represents the absolute permeability and porosity estimated from the logging tool. In this case the dot shown in Quadrant 1 is outside of the dotted lines representing +/−3 sigma variation. The expected trend in absolute permeability and porosity is from Quadrant 3 to Quadrant 2. The logging tool estimate in FIG. 4 is not in Quadrant 3 or Quadrant 2 and it is outside of statistically expected variation. Therefore, the logging tool estimates may be considered questionable as the result of an error such as trapped drilling mud in the rock pores or leakage in the seal of the logging tool and the well bore. A similar conclusion can be drawn if the logging tool estimate is in Quadrant 4 and falls outside of the +/−3 sigma variation. If the logging tool estimate falls in Quadrant 3 or Quadrant 2 and is outside the +/−3 sigma statistical variation, then the logging tool estimate may indicate a different lithofacies or other variation in the formation not present in the micro-sample extracted using the logging tool.

Figure 25:
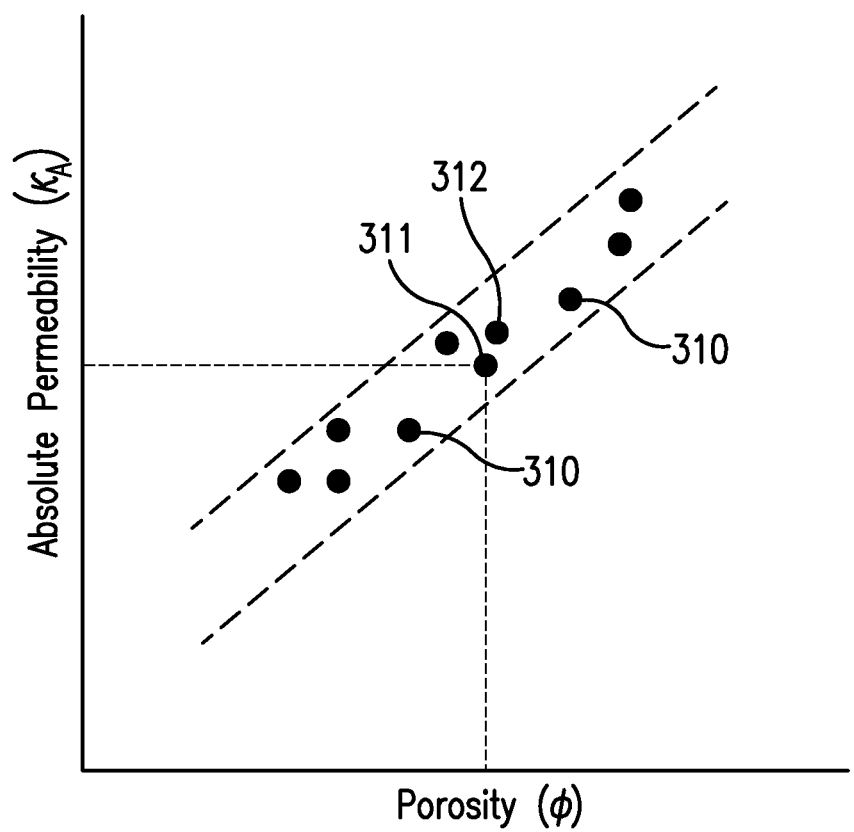
FIG. 25 is a plot of absolute permeability ($k_A$) versus porosity ($\phi$) for several digital sub-samples and a corresponding absolute permeability-porosity measure from a logging tool.

The present invention also comprises a method to select the digital rock analogue that is most representative of a facies, well, or formation. FIG. 25 shows a graph of absolute permeability ($k_A$) versus porosity ($\phi$). The graph includes points shown as the shaded circles, other than black circle 311, which are produced from digital rock physics using the Trend Method (310). Each of these points is produced from a sub-sample of the digital rock analogue using digital rock physics techniques. These points cover a wide range of porosity and absolute permeability. Digital rock physics is usually based on small sample sizes. As indicated, sub-sampling even the small samples can yield useful information about the range of rock properties in the formation or well, and the sub-sampling produces a range of data points, such as for absolute permeability versus porosity. Based on digital rock physics alone, it can be difficult to know which of these points is representative of a larger volume such as a lithofacies. Digital rock physics alone cannot identify which of the sub-samples is most representative of a facies, well or formation, at least not with levels of accuracy that may be specified or needed. In FIG. 25, the point shown as a black circle (311) is the measure of absolute permeability and porosity obtained from the logging tool (e.g., an MDT tool). The logging tool estimates absolute permeability and porosity from a larger volume in the well bore than the sample obtained for digital rock physics. The flow of fluids into the logging tool represents vertical permeability and horizontal permeability. The MDT tool, for example, makes an estimate of absolute permeability by doing a test based on the area of a couple of square centimeters, which is larger than any subsample. In addition, the MDT pressure test draws fluid from an even larger volume around to a location where the tool touches the well bore. The fluids may be drawn into the logging tool from a distance of several millimeters, several centimeters, several decimeters or a meter or more. The point (311) therefore is a measure of the porosity and absolute permeability obtained from a larger and more representative volume of the rock in a facies, well, or formation. The absolute permeability/porosity data (large volume) obtained with the logging tool can be compared with the digital values calculated for the sub-samples (small volume), and the sub-sample which is closest to the MDT values can be selected. In this way, the sub-sample which is most representative of a larger volume can be selected. For example, the digital rock physics point (312) closest to the measure from the logging tool was generated from a sub-sample that has rock properties similar to the logging tool point (311). This selected digital rock physics point (312) can be used in subsequent digital rock physics calculations such as relative permeability, capillary pressure, elastic modulus, formation factor, and other properties of interest. This approach to selecting a digital rock analogue can resolve a conflict in that a small sample size is necessary for CT scanning but a small sample size may not be representative of a large volume of the well bore. Further, a benefit of the present method is that the indicated selected sub-sample can be used for subsequent calculations with a higher degree of confidence that the calculations are representative of a significant portion of the well.

The present invention also comprises databases of deviations of logging tool rock property estimates for various formation types compared with the Trend Method curves produced with digital rock physics. These databases are constructed such that subsequent logging tool estimates of rock properties can be corrected in real time or near real time during the logging process.

The present invention further comprises simulation of a logging tool pressure transient test using the segmented digital rock physics model produced on the sample of rock retrieved by the logging tool as described above. The actual transient pressure response is compared to the calculated response and a confidence factor is assigned to the logging tool transient pressure test. In this way, erroneous data, such as when the logging tool does not form a secure seal with the well bore, is detected and erroneous data can be discarded.

Figure 5:
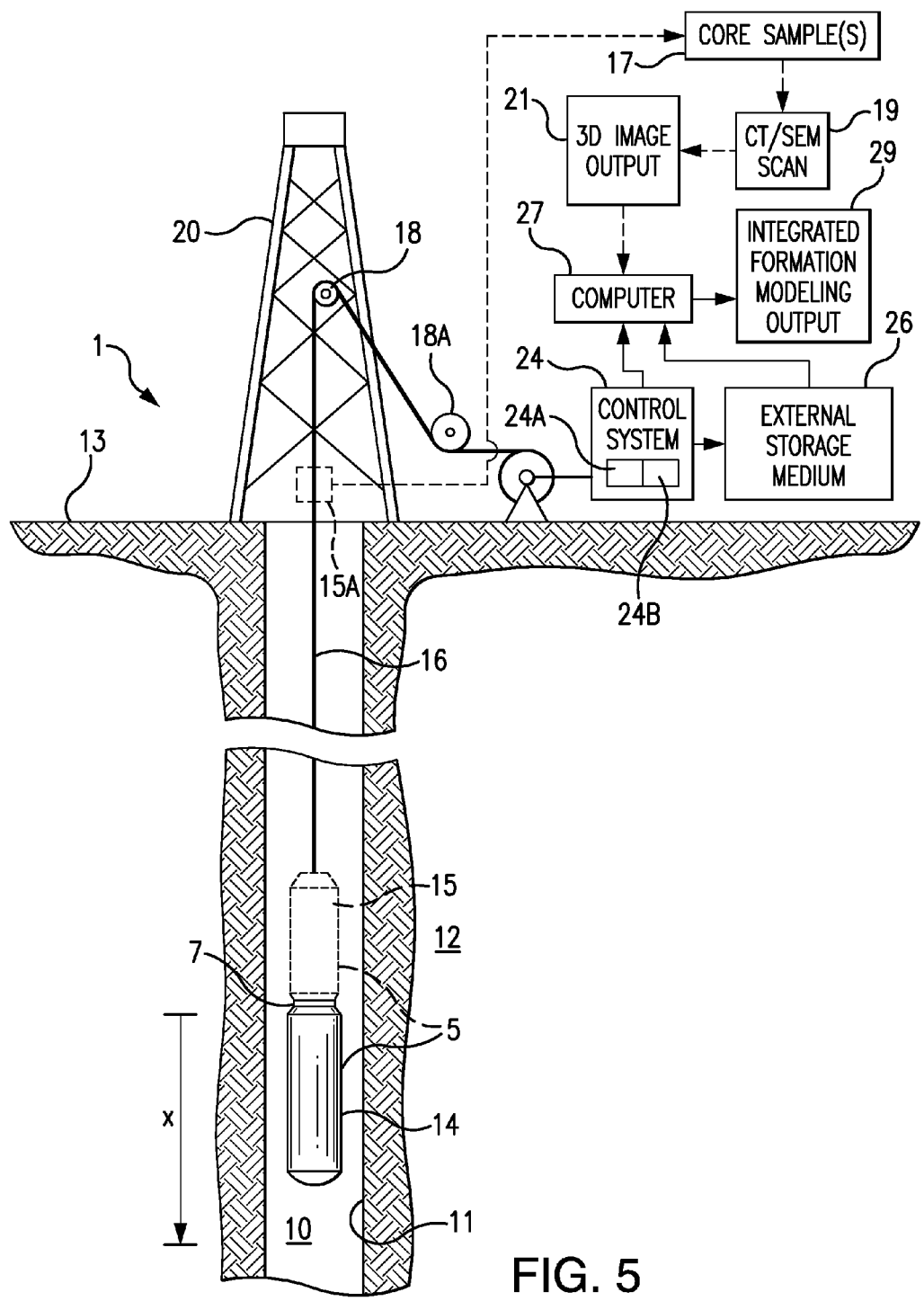
FIG. 5 is a cross-sectional view of a system for integration of well logging and in situ condition analysis when an MDT tool is deployed in a well bore at the well interval or intervals of interest, and core sample retrieval and 3D scan imaging analysis of a retrieved rock sample or samples from the same well interval or intervals, according to the present invention.

Referring to FIG. 5, a system 1 for in situ well logging and retrieving core samples from a formation for integrated 3D image analysis is shown. A well borehole 10 is shown penetrating earth formation 12, which has an upper surface 13. The well borehole 10 is drilled before formation evaluation tools are lowered into the borehole. Typically, the borehole 10 contains a combination of fluids such as water, mud filtrate, formation fluids, etc., which is not shown to simplify the illustration. For sake of simplifying the illustration, the rig 20 is shown as assembled directly on a dry land surface 13. A tool string 5 can be conveyed into and out of the borehole 10 with a wireline 16. An MDT tool 14 and core sample collection tool 15 are combined on the same tool string 5 in a vertically stacked formation in this illustration. Tools 14 and 15 are shown connected with a field joint 7. One of tool 14 or tool 15 is shown in solid lines and the other in broken lines in FIGS. 5 and 6 to emphasize which tool is located in a well interval "x" or well/formation depth of interest at that time. It will be understood that rig 20 alternatively can be mounted on an offshore drilling platform in a body of water (e.g., ocean, sea), wherein surface 13 would be the seabed or ocean floor, and piping (not shown) could extend from the rig 20 through an intervening body of water to the borehole 10 in the sea or ocean bed (13) through which tools 14 and 15 could be conveyed on before reaching and entering into the borehole 10. An MDT tool 14 or other in situ formation test tool useful for well logging is shown being lowered into the well borehole 10 on tool string 5 attached to an armored, multi-conductor cable or "wireline" 16. The tool 14 can be used to analyze the formation 12 at least through well interval "x" of the well borehole 10. The well interval "x" may be selected, for example, to be at a depth proximate to a known or possible reservoir of interest for in situ logging and retrieval of core samples for 3-D imaging as part of some of the present methods. The vertical distance of well interval "x" can vary depending on the particular site. The well interval "x" may be, for example, from about 10 feet to about 2,000 feet, or from about 25 feet to about 1,000 feet, or from about 50 feet to about 500 feet, or other distances. The tool 14 can be cylindrically-shaped in cross-section, or have another cross-sectional geometry sized to fit within the space bounded by the borehole wall 11 defining the borehole 10 and forming part of formation 12, for substantially unobstructed vertical movement of tool 14 up and down the borehole at the well interval or intervals of interest for in situ measurements and sampling and the borehole space above that location(s). Location 15A above the external surface 13 surrounding the borehole 10 can be where core samples or other formation samples, such as obtained with a different tool 15 shown in broken lines in FIG. 5, are retrieved for ex situ 3D image analysis, lab analysis, and/or other analysis relative to the borehole 10. In this non-limiting illustration, tools 14 and 15 are run on a single wireline 16. Although advancement of the tool 14 and tool 15 in the borehole 10 is shown using only a wireline 16 in a substantially vertically-oriented borehole 10 in the illustrations of FIGS. 5 and 6, other tool string conveyance systems may be used. A conventional or otherwise suitable tough logging conditions system (TLC), pipe-conveyed descent system, coiled tubing system, or downhole tractor system (not shown) known in the industry may be adapted for use in conveying tools 14 and 15 to the well interval of interest for downhole logging and core sample retrieval operations. For example, a specialized delivery system may be helpful or needed such as where the well interval of interest is in a segment of the borehole which is non-vertical.

Formation tester tool 14 can be, for example, an MDT tool capable of downhole characterization of formation fluids. The MDT tool can be capable of such downhole characterization of formation fluids without the need for transfer of fluid samples from below the surface to a laboratory for surface analysis. Tool 14 can include, for example, a power module(s), power conditioning circuitry, tool control processors, sensors required for the measurement(s) to be made in one or more modules, fluid processing modules, and telemetry circuitry to transmit the information back up the wireline 16, or other components. The wireline 16 can be played out from a winch 22, such as manually controlled by an operator within a well logging truck or skid (not shown) or automatically. The wireline 16 can be lowered into the borehole 10 after passing over a sheave wheel 18, which is in turn supported by rig 20, and after passing under a lower sheave wheel 18A. As indicated, tool string 5 is attached to wireline 16. The wireline 16 can include conductors that provide for power, control signals to and control and data information from the MDT or other in situ formation test tool 14. The conductors can be connected to an electrical control system 24, which can generally include a control processor 24A operatively connected with the tool string 5. Logging tool and sample collection operations forming parts of methods of the present invention can be embodied in a computer program that runs in the processor 24A. In operation, the program can be coupled to receive data, for example, from the downhole fluid analysis module(s), via the wireline 16, and to transmit control signals to operative elements of the borehole tool string 5. The computer program may be stored on a computer usable storage medium 24B (e.g. a hard disk) associated with the processor 24A, or may be stored on an external computer usable storage medium 26 or other recorder and electronically coupled to processor 24A for use as needed. The storage medium 26 may be any one or more of presently known storage media, such as a magnetic disk fitting into a disk drive, or an optically readable CD-ROM, or a readable device of any other kind, including a remote storage device coupled over a switched telecommunication link, or future storage media suitable for the purposes and objectives described herein. For example, the logging data stored at the storage medium 24B or external storage medium 26 can be transferred to one or more computers 27 having program instructions for carrying out further analysis of the logging data, 3D image analysis, and/or subsequent integrated formation property modeling as described herein. The computer or computing system 27 may include one or more system computers, which may be implemented as a personal computer or server. However, those skilled in the art will appreciate that implementations of various techniques described herein may be practiced in other computer system configurations, including hypertext transfer protocol (HTTP) servers, handheld devices, multiprocessor systems, microprocessor-based or programmable consumer electronics, network PCs, minicomputers, mainframe computers, and the like. The control system 24, the external storage medium 26, and computer 27 can be connected to each other for communications (e.g., data transfer, etc.), via any of hardwire, radio frequency communications, telecommunications, internet connection, or other communication means. Further, the data and other logging related information collected at the control system 24 and/or storage medium 26 may be visually displayed on a monitor, CRT, log chart, or other visual means of display (not shown) at the site and/or offsite. The tool data and any initial interpretation information thereon can be communicated, for example, via satellite or land lines (not shown) to an offsite or remote location for further analysis relevant to logging information or formation characterization, including other interpretation software in combination with 3D image data obtained from samples collected in the same well interval of the well bore.

Figure 6:
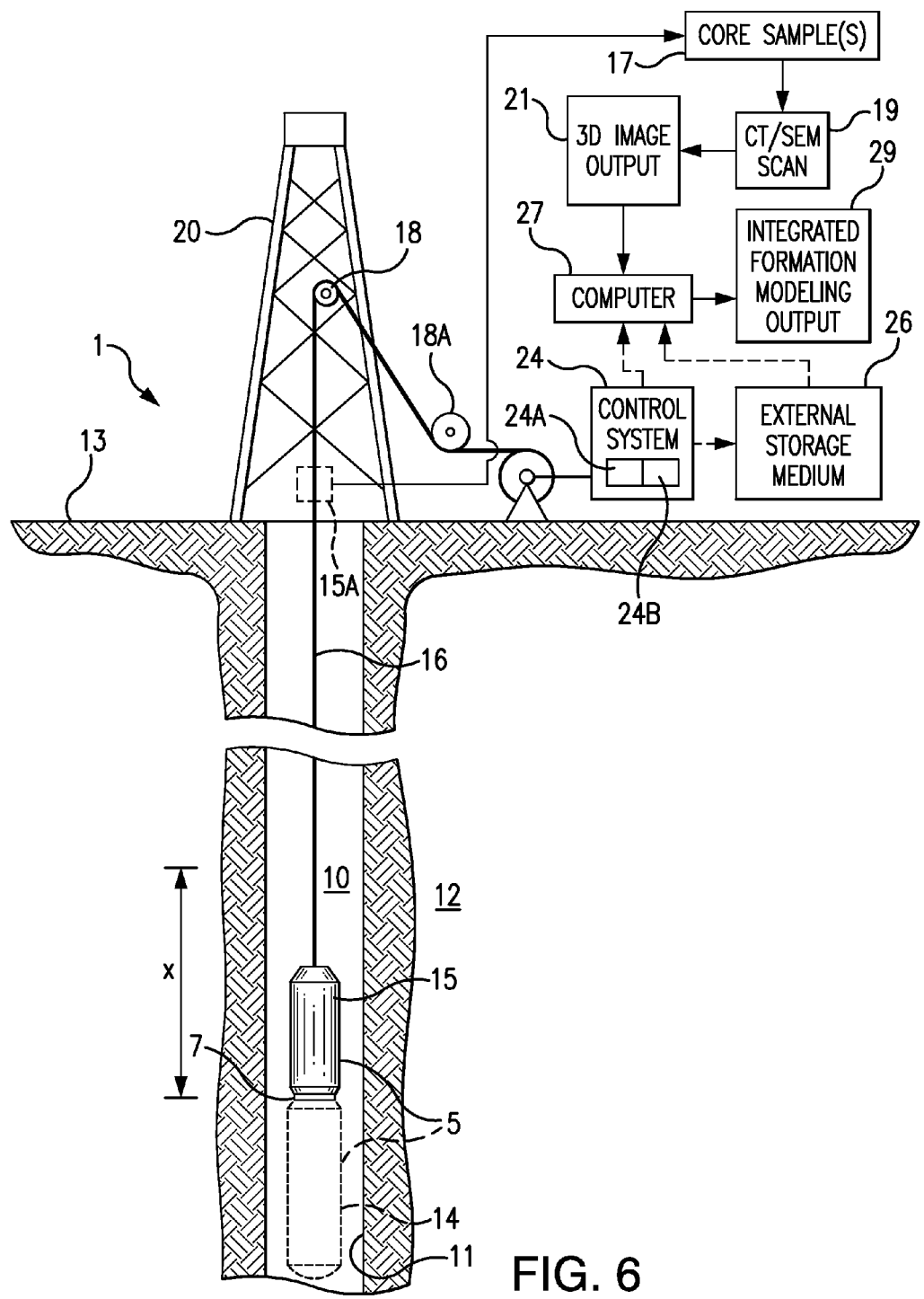
FIG. 6 is a further cross-sectional view of the system of FIG. 5 showing the system when a core sample retrieval tool is deployed in the well interval of the well bore according to the present invention.

As shown in FIG. 6, a core sample retrieval tool 15 can be lowered with tool string 5 on wireline 16 into the well borehole 10 for retrieval of core samples 17 from the formation 12, at least in the well interval "x" where in situ well conditions are being logged by tool 14 in the same or different run or pass. Tool 15 differs from any fluid sample extraction functionality of MDT tool 14 in that tool 15 is adapted to extract core plugs or other solid containing forms of samples from the formation, such as from the sidewall thereof. Retrieved core samples 17 can be collected from the tool 15 for 3D image analysis after it is lifted out of the well borehole 10 and above external surface 13, such as indicated by position 15A of tool 15 in FIG. 6. As shown in FIG. 6, core samples 17 (or other types of formation samples) removed from the formation 12 using core sample retrieval tool 15 can be transported to a computer tomographic ("CT") or SEM scanner 19. Tool 15 can include, for example, a power module(s), power conditioning circuitry, tool control processors, a remotely controllable rotary core or percussion sampling module, and telemetry circuitry to communicate via cable 16, or other components. The CT scanner or SEM scanner can use x-rays for analysis of internal structure of the samples, for generation of three dimensional (3D) images 21 of the core samples or other forms of samples retrieved from the formation. The images so generated can be in numerical form and their content will be further explained below. After scanning, the samples can be saved for further analysis or may be discarded. In general, the instrument used to scan the core samples 17, or other types of retrieved samples from the formation (e.g., percussion samples, cuttings, etc.), can be selected based on how small are the pores in the rock and how much resolution in needed to produce a usable image. Examples of suitable CT scanners for making images usable with methods according to the present invention, include, for example, 3D tomographic x-ray transmission microscopes, such as MicroXCT-200 and Ultra XRM-L200 CT, which are made by Xradia, Inc. (Concord, Calif. USA). For coarser samples, such as carbonates or sandstones, the MicroXCT-200 may provide sufficient resolution. When smaller pore samples, such as some shales, are tested, the higher Ultra XRM L200 CT may be useful. In addition, very dense rock formations, such as some shales, can require resolution beyond X-ray CT scanners. In these situations, scanning electron microscopes can be used instead. An example of an SEM than can be used is Zeiss Auriga SEM. In the present example, the 3D image output (images) 21 generated by the CT scanner 19 can be transferred to a computer 27 having program instructions for carrying out the indicated logging data analysis, the image analysis, and subsequent formation property modeling to provide formation modeling output/results 29, as described below.

Multiple tools can be lowered on wireline 16 down the borehole 10 for logging and sample retrieval, and possibly other operations (e.g., CMR analysis), in combination on the tool string 5 in a single run, or in separate runs. In FIGS. 5 and 6, the MDT tool 14 and core sample retrieval tool 15 can be combined, for example, in one run down the borehole 10, even though the tools are operated sequentially. The tool 14 and 15 can be provided as separate modules which are operatively connected together with a field joint or connector 7. The field joint or connector may provide an electrical connection, a hydraulic connection, a flowline connection, or combinations of these, depending on the needs of the tools on the wireline. Field joints are shown, for example, in U.S. Patent Application Publication Nos. 2006/0283606 A1 and 2009/0025926 A1, and U.S. Pat. No. 7,191,831, which are incorporated herein by reference in their entireties. As indicated, the formation test tool 14 and the core sample retrieval tool 15 can be combined on a single tool string 5 lowered on a single wireline 16 into the well interval "x" of interest. As shown in FIGS. 5 and 6, tools 14 and 15 can be sequentially advanced into the well interval "x" of interest for in situ downhole property measurements or core sample collection, respectively. Alternatively, tool 15 can be located below tool 14 on tool string 5. Although not illustrated in FIGS. 5 and 6, the logging tool 14 may comprise an MDT tool which integrally incorporates at least one core sample retrieval module within a common housing. These various options for deploying tools 14 and 15 share the method of using both at least an MDT tool for in situ logging information collection in a selected well interval, and a sample retrieval tool (separate from or integrated with the logging tool) for extraction of samples over the same well interval from the wellbore for 3D image scanning and analysis outside the well borehole and formation. Other formation analysis tools, such as a combinable magnetic resonance (CMR) tool (not shown), may be combined in the tool string in the same or separate runs with respect to the MDT tool and core sample retrieval tool. The number of tools that may be included in any single run versus using multiple runs over the same well interval may be influenced by a number of factors, including compatibility, power consumption, and telemetry requirements, and other factors.

Figure 7:
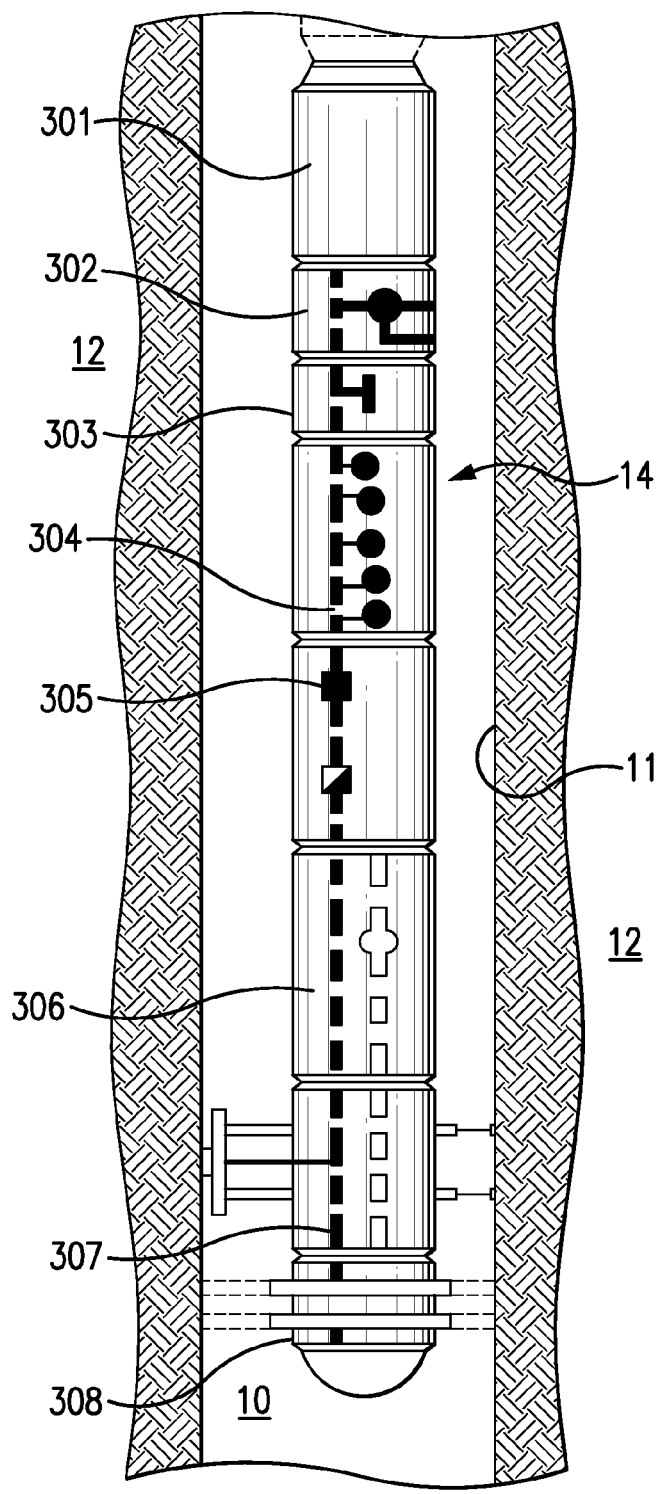
FIG. 7 is a cross-sectional view of an MDT tool of FIG. 5 when deployed in the well borehole according to the present invention.

FIG. 7 is an enlarged view of an MDT tool 14 configured in a modular format. As noted above, the MDT or other in situ formation test tool 14 can be lowered on armored cable 16 to the interval or zone of interest "x" where in situ formation analysis (and core sample retrieval for ex situ 3D imaging analysis), is desired. In the instance of a formation test tool, the tool 14 can be stationary when it makes its measurements, or moving, depending on the type of measurement. The MDT formation test tool 14 in FIG. 7 is shown as being comprised of several modules 301-308. The modules 301-308 of tool 14 can be joined to each other using field joints (not shown). The sensor and testing devices of tool 14 alternatively can be assembled within a common housing. Modular tool tester designs can permit the user to customize and configure the tool 14, including on-site, to meet requirements depending on the needs of a particular well evaluation. Accordingly, a lesser or greater number of modules can be combined into tool 14. As indicated herein, a number of in situ formation and well borehole conditions can be used in various present methods. Accordingly, the MDT tool can be customized in modular form to provide evaluations for those and other in situ parameters of interest. In this regard, Table I shows several exemplary logging tool configurations 1-5 of modules of tool 14 with respect to FIG. 7, which, as indicated, can include all modules 301-308 or lesser combinations thereof. Some module parts of configuration 5, for example, are illustrated schematically in FIG. 7, while other different types of modules of other configurations are not shown to simplify the illustrations.

TABLE I

| Module Number | Logging Tool Config. 1 (module type) | Logging Tool Config. 2 (module type) | Logging Tool Config. 3 (module type) | Logging Tool Config. 4 (module type) | Logging Tool Config. 5 (module type) |
|---|---|---|---|---|---|
| 301 | Power | Power | Power | Power | Power |
| 302 | Hydraulic | Hydraulic | Pump-out | Multisample (fluid) | Pump-out |
| 303 | Single-probe | Single-probe | Hydraulic power | Sample chambers (fluid) | Sample chambers (fluid) |
| 304 | Single-probe | Single-probe | Single-probe | Pump-out | Multisample (fluid) |
| 305 | Sample chambers (fluid) | Dual-probe | Dual-packer | In situ live fluid analyzer | In situ fluid analysis module |
| 306 | Sample chambers (fluid) | Flow-control | Flow-control | Hydraulic power | Hydraulic Power |
| 307 | None | Sample chambers (fluid) | Sample Chambers (fluid) | Single-probe | Single-probe |
| 308 | None | None | None | None | Dual-packer |

Other combinations of these and other MDT modules in formation tester tools can be used, provided the resulting tool configuration can be sufficient to collect the requisite in-situ data from the well borehole and formation for the present methods. A commercial supplier of such MDT formation tester tools (Schlumberger), has characterized a modular tool configuration similar to Configuration 1 as a basic MDT for pressure, permeability, and fluid sampling, Configuration 2 as a multi-probe vertical interference testing, Configuration 3 as vertical interference testing with a probe-packer, and Configuration 4 as low shock PVT-quality sampling. Tools similar to Configuration 5 are described in greater detail, for example, in U.S. Patent Application Publication No. 2009/0078036 A1, which is incorporated herein by reference in its entirety. As indicated, other combinations of these or other known MDT modules may be used. Other commercially available devices which may be adapted for use as tool 14, include, for example, a Reservoir Characterization Instrument (RCI) of Baker Atlas.

Illustrative details on the equipment and functions of the modules indicated in Table I can be understood from various commercial MDT tools. Downhole fluid analysis can be done using one or more fluid analysis modules in an analysis module, for example, Schlumberger's Modular Formation Dynamics Tester (MDT). The power module of the MDT tool can be, for example, an electric power module which can convert AC power from the surface to provide DC power for all modules in the tool. The hydraulic power module, for example, can contain an electric motor and hydraulic pump to provide hydraulic power for setting and retracting the single- and dual-probe modules. The single-probe module can contain, for example, a probe assembly with packer and/or backup pistons, and can include, e.g., pressure gauges, fluid resistivity sensors, temperature sensors, strain gauge, a pretest chamber, and so forth. The volume, rate and drawdown of the single-probe module can be controlled from the surface to adjust to the test situation. The dual-probe module can contain, for example, two probes mounted back-to-back and approximately 180° apart on the same assembly body. When combined with a single-probe module, the dual-probe module can form a multi-probe system capable of determining horizontal and vertical permeability. During a typical test with the dual-probe module, formation fluid can be diverted through a sink probe to a pretest chamber (not shown) in a flow control module. The dual-probe module, in conjunction with the pressure measured at the vertical probe from the single-probe module, can measure the pressure at both probes, and these measurements can be used, for example, to determine near-wellbore permeability anisotropy. The dual-packer module can use multiple inflatable packers, set against the borehole wall, to isolate and seal a section of the formation (e.g., about 2 to about 15 feet, or about 3 to about 12 feet, or other section lengths), and provide access to the formation over a wall area to allow fluids to be withdrawn without dropping below the bubble point, and it can provide a permeability estimate. The dual-packer module can be used to make pressure measurements and take fluid samples, and can be used for in-situ stress testing and mini-frac testing. The pump-out module can be used to pump unwanted fluid (e.g., mud filtrate) from the formation to the borehole, so representative fluid samples can be taken, and it also can be used to pump fluid from the borehole into the flowline for inflating the packers of the dual-packer module, and also can pump within the tool, for example, from a sample chamber to the inflatable packers. Further, as known in the field, a formation field sample essentially free of contamination from the drilling mud filtrate may be provided by using dual pumps to withdraw both the reservoir fluid and the surrounding mud filtrate simultaneously into separate flowlines, to divert the mud filtrate into the borehole while a relatively purer stream of formation fluid can be obtained for measurement and collection in real time. The live fluid analyzer, which may be used in combination with the pump-out and dual inflatable packers, can be used to provide downhole fluid analysis in real time. The live fluid analyzer can measure optical properties of the fluid in the flowline, and can employ an absorption spectrometer that utilizes visible and near infrared light to quantify the amount of reservoir and drilling fluids in the flowline. Another sensor in the live fluid analyzer can be a gas refractometer, which can be used to differentiate between gas and liquid in known manners. The fluid analysis module can be, for example, a live fluid analyzer, an optical analyzer, or ultra fluid analyzer, such described, for example, in U.S. Patent Application Publication No. 2009/0078036 A1, which is incorporated herein by reference in its entirety. An ultra fluid analyzer, for example, can be used for flowing and captured analyses of downhole fluid samples to provide compositional and physical property measurements, such as density, viscosity, and the like. The flow control module can be a pretest chamber where the flow rate can be accurately measured and controlled, and it can be used during sampling that requires a controlled flow rate. The flow control module can create a pressure pulse in the formation large enough for multiprobe measurements. The sample and multisample chambers can be designed to retrieve two or more formation fluid samples during a single run into the well for laboratory analysis outside the well. As indicated, use of MDT tool modules having operability for downhole characterization of formation fluids, such as the live fluid analyzer, optical fluid analyzer, or ultra fluid analyzer. Additional sensors for fluid and formation characterization, e.g., NMR imaging sensors, acoustic sensors, or other sensors may be located in any of the modules of formation test tool 14. Other details on these and related modules are described, for example, in U.S. Patent Application Publication No. 2009/0079036 A1 and U.S. Pat. No. 6,856,132, which are incorporated herein by reference in their entireties.

In using MDT tool 14, the tool can be lowered to a desired test depth within the borehole 10. Modules having pistons, back-up shoes, and/or inflatable packers or similar devices can be actuated to move the tool 14 into a vertically-stationary position relative to the borehole wall 11, to restrict or block some fluid movements within the borehole, and so forth. It will be appreciated that the test program can vary with the parameters to be measured, the nature of the formation 12, and the number of samples taken for in situ evaluation. After completion of the desired in situ measurements, the tool 14 can be deactivated and the pistons/inflatable packers returned to the retracted/deflated positions/states, and the tool 14 may then be moved to a different depth for additional testing or returned to the surface 13 after completion of all tool operations. For example, after moving tool 14 out of the well interval "x", tool 15 can be moved into position in the same well interval "x" for core sampling, or vice versa.

Figure 8:
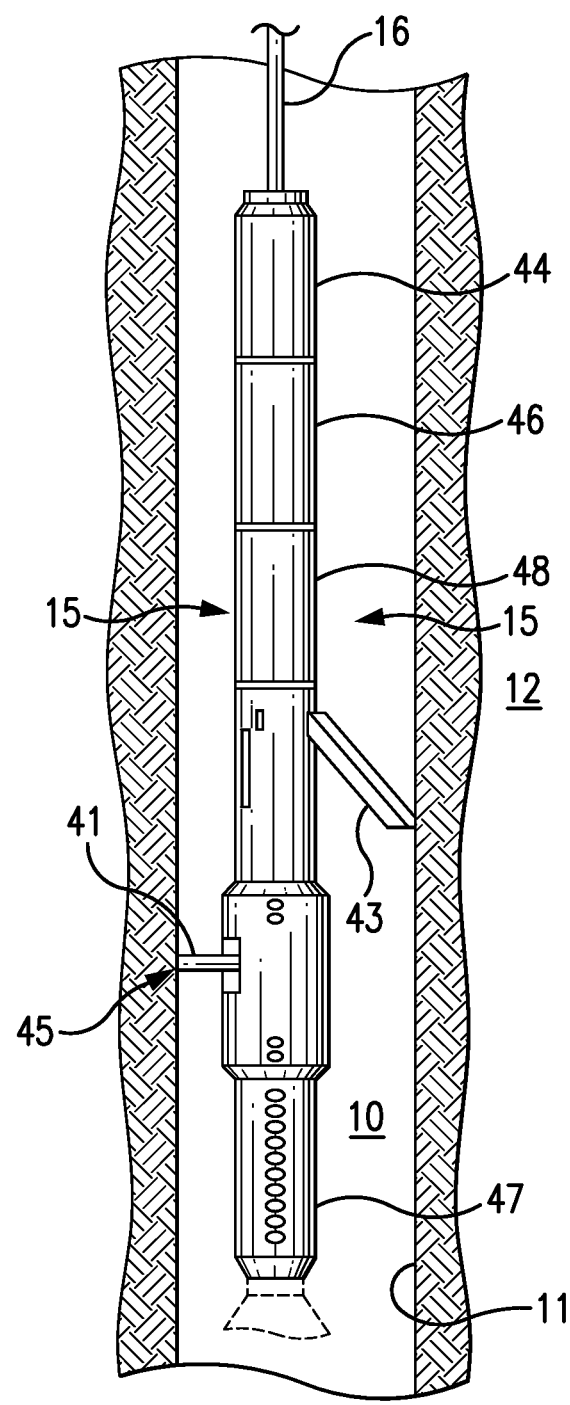
FIG. 8 is a partial fragmentary side view of a sidewall rotary coring tool used for the sample retrieval tool shown in FIG. 6 when deployed in the well borehole according to the present invention.

Referring again to FIG. 6, the core sampling done by tool 15 can be, for example, sidewall coring or percussion. In sidewall coring, the wireline coring tool can be run into the hole in the same run when the well is logged with tool 14 or in a separate run. The sidewall coring tool can be operable, for example, for sidewall rotary coring or percussion type core sampling. In more detail in FIG. 8, tool 15 is shown as a sidewall rotary coring tool having a small extendable/retractable robotic core bit 41 or other drill bit device having similar functionality, which can be used to bore a core sideways into the formation. The drill bit 41 can be, for example, a horizontal hollow rotary diamond drill bit. The drill bit can be hollow tubular-shaped defining a receiver tube with diamond cutting edges surrounding the distal opened end thereof. The drill bit can be rotated, for example, at about 2,000 rpm or higher. A backup shoe 43 or similar device can be extended and used opposite the rotary drill bit of the tool to hold or brace the tool 15 securely against an opposite wall 11 of the formation 12. Alternatively, an inflatable packer module can be used to hold the core sampling tool 15 in place during sidewall coring. The core sampling tool 15 also can include additional modules or components, which can be commonly used in sidewall coring tools of this type, such as, for example, an electronics control and power module 44, a compensator module 46, and hydraulic module 48, which can be configured in conventional or commercially known manners. In a sample collection mode of operation of tool 15, a cut core sample 45 is captured in the hollow interior of the drill bit 41 from the sidewall drilling, which core sample can be broken loose from the formation, such as, e.g., by slight vertical movement of the drill bit 41, and withdrawn into the coring tool 15 for retrieval from the borehole. For example, the core sample can be punched into a receiver compartment 47 (e.g., tube) of the tool 15. Then, the tool 15 may be moved to another spot in the well interval or intervals of interest within the borehole, and the bit can be extended and used again to retrieve another sidewall core sample, and so on, until the desired number of cores are retrieved from the desired locations. Alternatively, a single core sample can be retained in the hollow bit for retrieval after the tool is pulled out of the borehole. Each sample can be isolated for identification, for example, including recording of data on the formation location (e.g., borehole depth, core depth), and time. The core can be recovered as a small cylindrical-shaped plug of the formation. The core samples obtained with the rotary sidewall coring tool can be, for example, about one inch (25 mm) or less in diameter by about 1-2 inches (25-51 mm) or less in length, or smaller, such as about 2 mm or less in diameter by about 2 mm or less in length.

As indicated, rotary cores are only one type of rock formation sample that may be analyzed according to methods of the present invention. Percussion sidewall core samples may be obtained using tool 15 on tool string 5 for withdrawal from the well borehole 10 as part of the wireline well evaluation techniques. The percussion method, if used for sample collection, can use, for example, a high explosive charge to propel a short core barrel into the formation at high speed to embed the core barrel into the formation rock, and then the core barrel is withdrawn by a strong wire. Typically, cores of about 1 inch (25 mm) or less in diameter and about 1-2 inches (25-51 mm) or less in length can be retrieved by this method. The core samples obtained using tool 15 and withdrawn from the borehole can then be 3-D imaged and analyzed in conjunction with well logging information and evaluations thereon in accordance with present methods.

Figure 9:
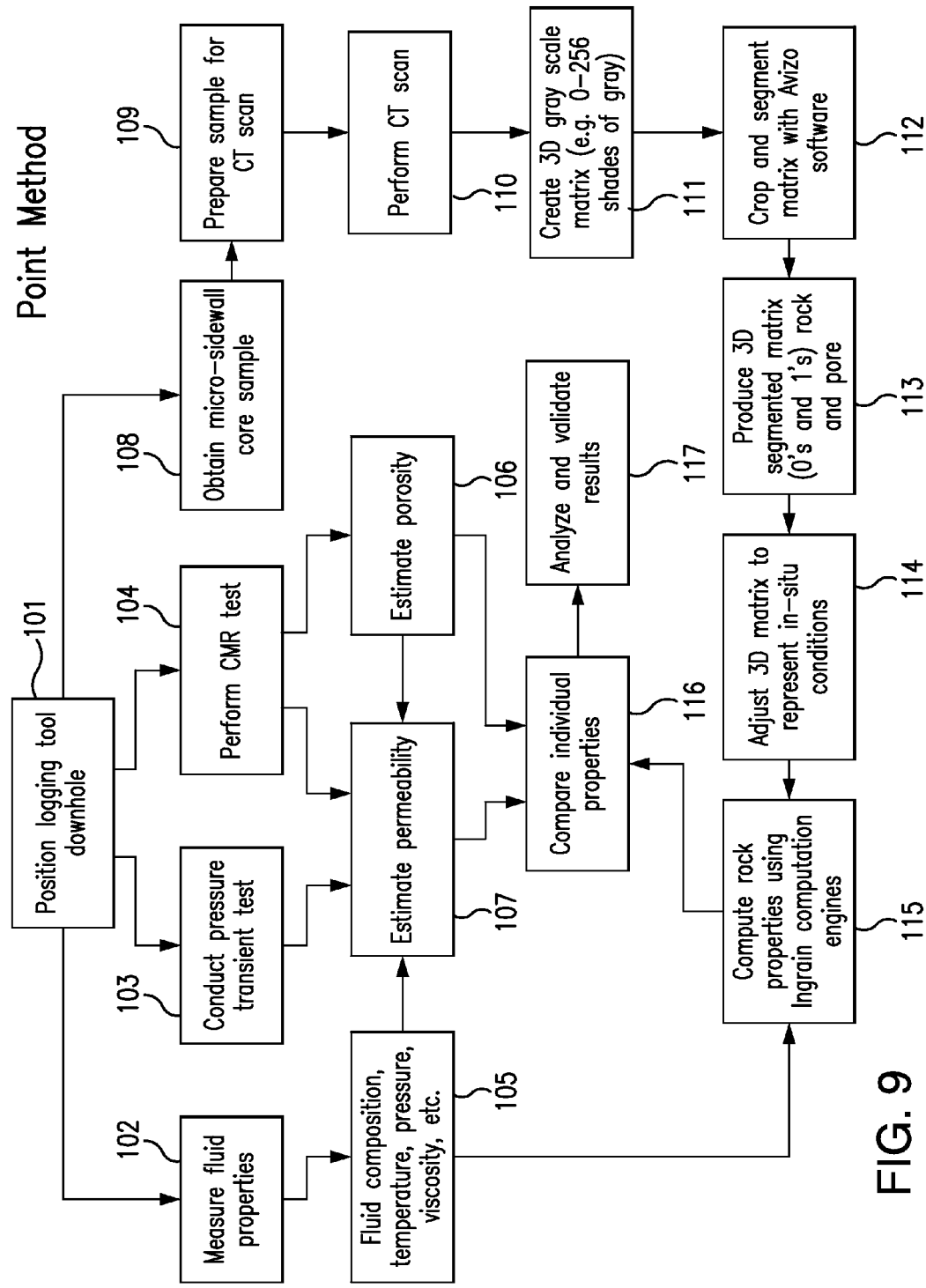
FIG. 9 is a flow chart of a Point Method for integrating logging tool and digital rock physics according to the present invention.
Figure 10:
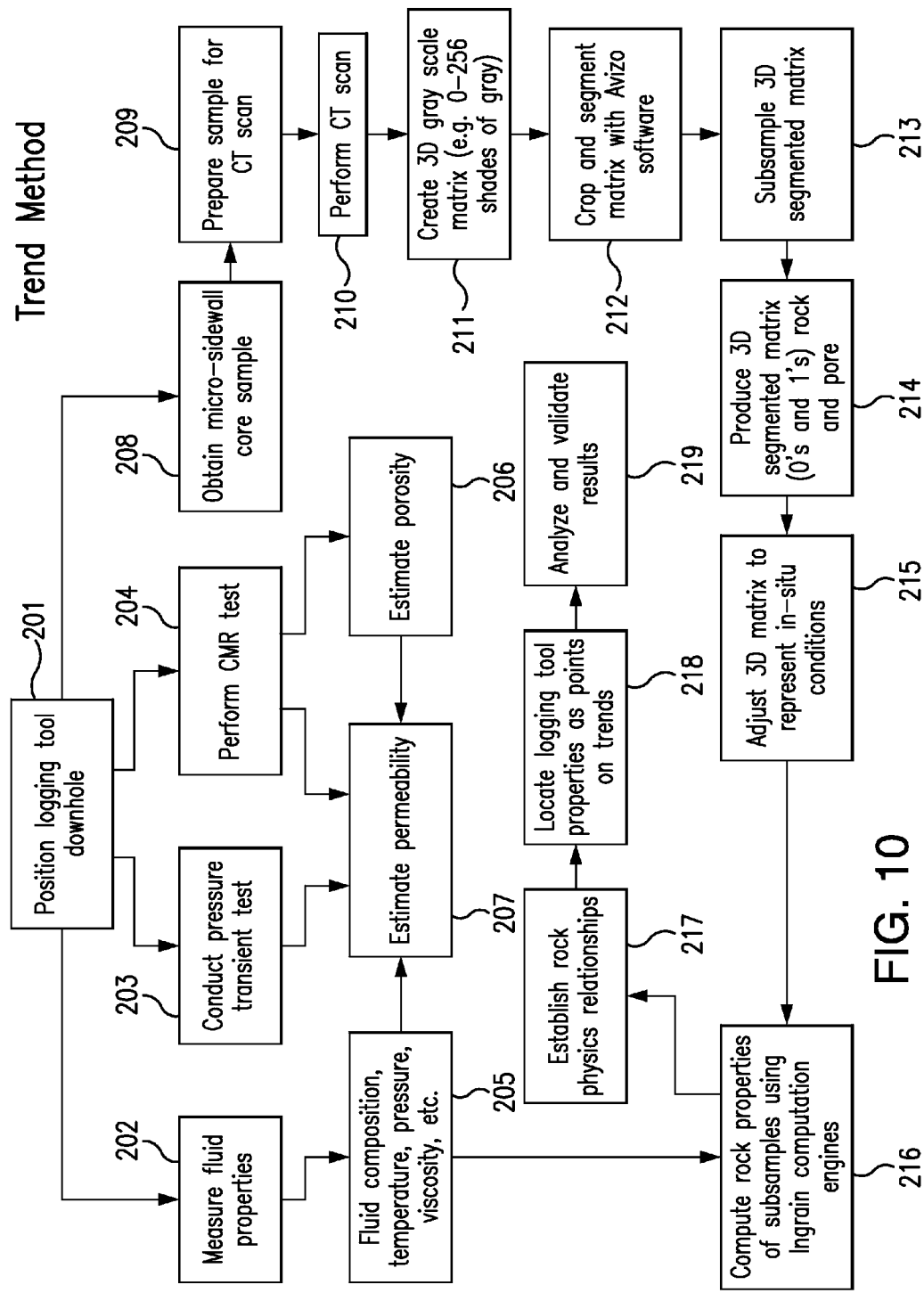
FIG. 10 is a flow chart of a Trend Method for integrating logging tool and digital rock physics according to the present invention.

Referring to FIGS. 9 and 10, examples of the indicated point method and trend method are shown in more detail with reference to steps 101-117 and 201-219, respectively.

Referring to FIG. 9, steps 101-117 of the point method can relate to methods and operations such as indicated in the following discussions.

Step 101

The lowering of a tool string carrying the formation tester tool on a wireline into a well borehole and positioning of a formation tester tool downhole in the well interval of interest for evaluation can be implemented in manners such as described with respect to FIGS. 5-8.

Step 102

Sensors and analyzers provided on tool 14 are used to take measurements in the well interval of interval of downhole fluid conditions, which can be downhole measurements which are processible to determine measures of downhole fluid properties (e.g., fluid composition, pressure, viscosity, etc.) which, in turn, can be used in estimating permeability in subsequent steps of the present method. The tool used to take these downhole measurements can be, for example, a logging tool similar to one or more of logging tool configurations 1-5 and the referenced patent/application publications.

Step 103

A pressure transient test can be performed in a known manner, for example, using a formation tester (e.g., Schlumberger Modular Dynamics Tester (MDT)), to measure the transient build up in the pore pressure following an extraction of a fixed volume of formation fluid. Under suitable assumptions of flow regime near the probe, the effective permeability ($k_e$) of the formation can be related to the pressure build up.

Step 104

A CMR test can be performed in a conventional manner, such as by taking NMR measurements with a formation tester having that capability, such as can be provided by the Schlumberger Combinable Magnetic Resonance tool known by the acronym CMR (or equivalents thereof). An example of methods of performing a CMR test which may be adapted to the present methods includes those shown in U.S. Patent Application Publication Nos. 2008/136410 A1 and 2011/0054796 A1, which are incorporated herein by reference in their entireties.

Step 105

Figure 1B:
Figure 1C:

Downhole measurements taken in step 102 using tool 14 are processed, such as at processor 24A and/or at computer 27 shown in FIG. 1, to provide measurements of fluid composition, temperature, pressure, viscosity, and/or other fluid properties.

As indicated in the discussion of step 102, various downhole fluid properties in the well interval of interest can be determined.

Step 106

Porosity can be estimated from the CMR test results of step 105 in any conventional manner applied for that purpose.

Step 107

Permeability can be estimated using formation data collected in steps 103, 104, 105, and 106. Known algorithms can be used (e.g., Darcy's Law). An example of a method of estimating permeability, which may be adapted to the present methods, includes that shown in U.S. Patent Application Publication No. 2011/0054796 A1, which is incorporated herein by reference in its entirety.

Step 108

As discussed in regards to FIG. 4, a micro-sidewall core sample can be obtained using sidewall rotary coring tool, such as disclosed herein, or other suitable coring methods.

Step 109

A sample can be prepared for scanning, the sample can be directly taken from a standard coring tool or it may be a "micro" sample (e.g., 2 mm diameter or less by 2 mm or less in length). Such micro samples typically are not taken in the industry currently because physical laboratories cannot test such a small sample. Digital methods, however, can handle a smaller sample. Taking a smaller sample can be an advantage, for example, when the rock formation is very tight and difficult to cut.

Step 110

Figure 2A:
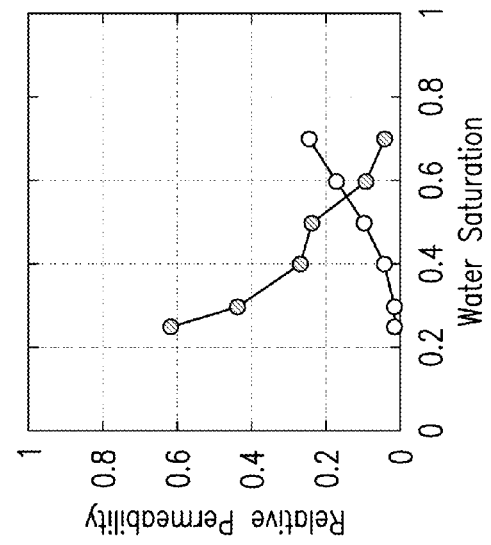
FIGS. 2A-B are plots showing relative permeability curves to water (grey dots) and gas (darker black dots) in the same sandstone sample, but with varying interfacial tension (from left to right).
Figure 2B:
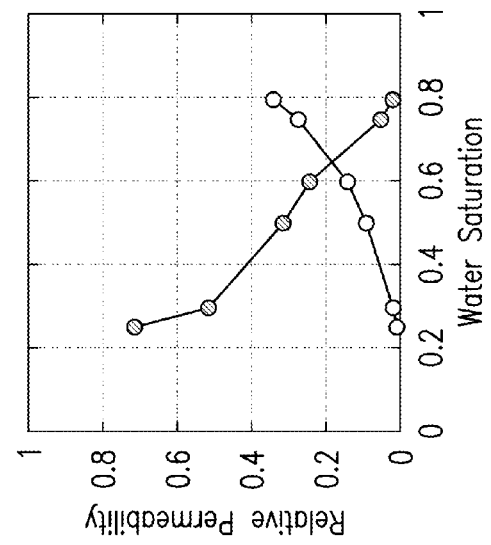

As discussed in regards to FIG. 2, a CT or SEM scan of the core sample retrieved from the well interval of interest can be performed. As indicated in the discussion of the CT/SEM scan in FIG. 2, one difference between the Xradia MicroXCT-200 and Ultra XRM-L200 CT is resolution. For coarser samples such as carbonates or sandstones, the scanner model MicroXCT 200 may provide sufficient resolution. When smaller pore samples, such as some shales are tested, the higher Ultra XRM L200 CT scanner may be useful. In addition, very dense rock formations, such as some shales, can require resolution beyond X-ray CT scanners. In this case, scanning electron microscopes can be used instead, such as a Zeiss Auriga SEM. In general, the SEM instrument used is selected based on how small the pores in the rock are and how much resolution is needed to produce a usable image. As indicated, the choice of scanner depends upon the size of the grains and pores in the rock sample. It is common that one scanner is used, but more than one scanner may be used if a low resolution scan is initially used to select an appropriate area on the rock for a higher resolution scan.

The voxel size of the images obtained with the CT or SEM scanner can depend on the type of scanner used and the resolution. For X-ray CT scanners (typically used for carbonates and sandstones) the voxel size can range, for example, from about 500μ (microns) to about 65μ. For scanning electron microscopes (SEM)(typically used for shales), the voxel size can range, for example, from about 20 nm (nanometers) to about 5 nm. The scanners typically output a series to two-dimensional arrays of values representing the gray scale values from the scanner. For X-ray CT scans, approximately 1024 scans, for example, can be used to produce the "stack" of "images". There is no technical reason why this number could not be changed. The resolution is determined by the thickness of the sample. The resolution is the thickness divided by 1024 in this case. For SEM scans, the resolution can be set at 5 nm and the number of scans can be adjusted depending on the thickness of the sample. Other resolutions such as 7.5 nm or 10 nm can be selected, for example, for SEM scans.

Step 111

Gray scale image creation of this step is produced from the arrays generated by the CT scanner in the previous step 110. The gray scale image creation of this step can be similar to the gray scale process in U.S. Patent Application Publication No. 2010/0128932 A1, which is incorporated herein by reference in its entirety.

The CT scan image output produced by a CT or SEM scanner, such as 3D image output 21 of scanner 19 in FIG. 2, can be a 3D numerical object consisting of a plurality of 2D sections of the imaged sample. Each 2D section includes a grid of values each corresponding to a small region of space defined within the plane of the grid. Each such small region of space is referred to as a "pixel" and has assigned thereto a number representing the image darkness (or for example the density of the material) determined by the CT scan procedure. The value ascribed to each pixel of the 2D sections is typically an integer that may vary between zero and 255 where 0 is, e.g., pure white, and 255 is pure black. Such integer is typically referred to as a "gray scale" value. 0 to 255 is associated with eight digital bits in a digital word representing the gray scale value in each pixel. Other gray scale ranges may be associated with longer or shorter digital words in other implementations, and the range of 0 to 255 is not intended to limit the scope of the invention. For the purpose of simulating a physical process using such a numerical object (the gray scale), however, the numerical object can be processed so that all of the pixels allocated to the void space in the rock formation (pore space) are represented by a common numerical value, e.g., by only 255s, and all of the pixels associated with the rock matrix (or rock grains) are represented by a different numerical value, for example, zeroes. Subsequently, the resulting numerical object can be normalized so that the pore spaces are represented by, for example, ones and the rock grains are represented by zeroes. The foregoing may be described as converting the image into a binary index. In other examples, the image may be converted into an index having any selected number, n, of indices. It has been determined that sufficiently accurate modeling of some rock petrophysical parameters or properties, e.g. permeability, may be obtained using a binary index, in which one value represents pore space and another single value represents rock grains.

Step 112

The gray scale image created in step 111 can be cropped and segmented. The cropping and segmentation step can be done with Avizo® software adapted for use in the present methods. Standard modules of Avizo® software can be used to process the arrays to do calculations for cropping the matrix. Avizo® Edition software, such as either the Avizo® Earth or Avizo® Fire options of the Avizo® standard product can be used for cropping the matrix. The screen menu options used for this purposes can vary. After cropping the matrix, the image is segmented. Program modules can be programmed into Avizo® software for executing this operation. The Aviso-based segmentation package uses various image-processing techniques that include (a) noise reduction; (b) identifying the boundaries of the grains based on 3D surface gradients of the gray scale encountered in the original image; and (c) thresholding based on this image enhancement and focus sharpening. Another segmentation process which can be adapted for use in the present methods is in U.S. Patent Application Publication No. 2010/0128932 A1, which is incorporated herein by reference in its entirety.

Step 113

A segmented 3D matrix is produced from the cropped and segmented matrix of step 112. Image segmentation provides a segmented 3D image of the rock sample including image elements for rock grain and for pore sizes. The 3D segmented image can be stored or displayed in a computer and can be used as input to one or more rock property characterization models. Another segmented 3D matrix process which can be adapted for use in the present methods is in U.S. Patent Application Publication No. 2010/0128932 A1, which is incorporated herein by reference in its entirety.

Step 114

In this step, two different types of adjustments can be made to the 3D matrix to represent in-situ conditions with respect to (1) introducing cracks in the 3D matrix cracks that exist in-situ which are not imaged, and to (2) closing image cracks generated due to unloading the core sample from the in-situ stress to benchtop stress.

With respect to these adjustments in the 3D matrix, to compute the in-situ values of porosity, permeability, and electrical resistivity of rock represented by its CT-scan or FIB/SEM image, elastic properties of the rock sample are first computed assuming that the mineral phase is pure quartz. If the result matches a theoretical in-situ-stress model where the elastic properties are calculated assuming that the rock is also pure quartz, it can be concluded that the image is relevant to the in-situ conditions and, hence, all other properties computed on this image are also likely to be relevant to the in-situ-stress conditions. If the elastic properties thus computed do not match the theoretical-model prediction, the image is processed to introduce or eliminate the compliant cracks that appear in the physical sample due to its unloading from the in-situ to benchtop stress. This can be accomplished either by altering an image or taking its subsamples. Once the elastic properties computed on the image thus processed (or some of its subsamples) match the above-mentioned theoretical criterion, it can be concluded that all other properties computed on the same image are valid at in-situ conditions as well.

The physical properties of rock vary with varying differential stress. The differential stress at in-situ conditions depends on the depth of burial, tectonic forces, and the pore pressure. It may be as high as 40 MPa (about 6,000 psi). At the same time, the CT-scan and FIB/SEM images of rock samples used in computational rock physics are taken at ambient (benchtop) conditions with essentially zero differential stress. The challenge becomes how to infer the in-situ rock properties from the images taken at benchtop conditions.

In meeting this challenge, four types of physical properties are considered: the total porosity; the elastic properties (the bulk and shear moduli and elastic-wave velocity); the absolute permeability; and the electrical resistivity. The variations of all these properties with stress are directly related to the changes in the pore geometry of rock. Usually, as a sample is brought from the subsurface, it expands resulting in porosity increase. However, the most important result of reducing the stress is that the pore space variations are not geometrically congruent. As shown in FIGS. 11A-B, new pores, such as very thin cracks, may open up on benchtop. Also, contacts between mineral grains that existed in-situ may relax or simply disappear on benchtop. Such new features appearing in the mineral framework generally weakly affect the total porosity. However, because these newly opened cracks are extremely compliant, they may strongly affect the elastic-wave velocity. The permeability behavior is somewhat different. In cases where robust flow paths exist in-situ, the addition of thin cracks due to stress reduction cannot significantly affect permeability. However, where permeability is small or non-existent in-situ and flow paths are exclusively dependent on cracks, additionally generated cracks may strongly increase permeability (in relative terms) and even make a sample impermeable in-situ permeable on benchtop. This usually occurs in tight gas sandstone and tight shale. The stress dependence of the electrical resistivity of porous rock is qualitatively similar to the permeability behavior.

Figure 12B:
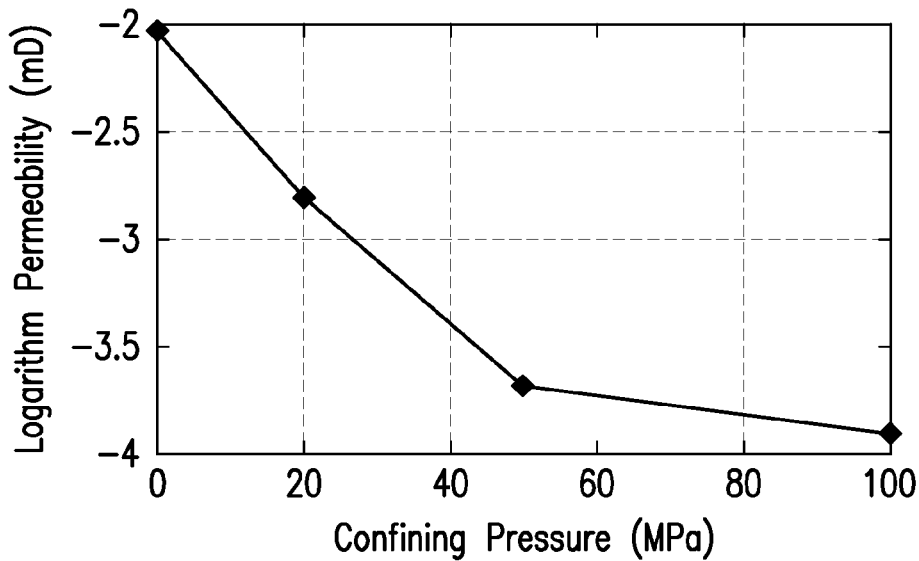
Figure 12C:
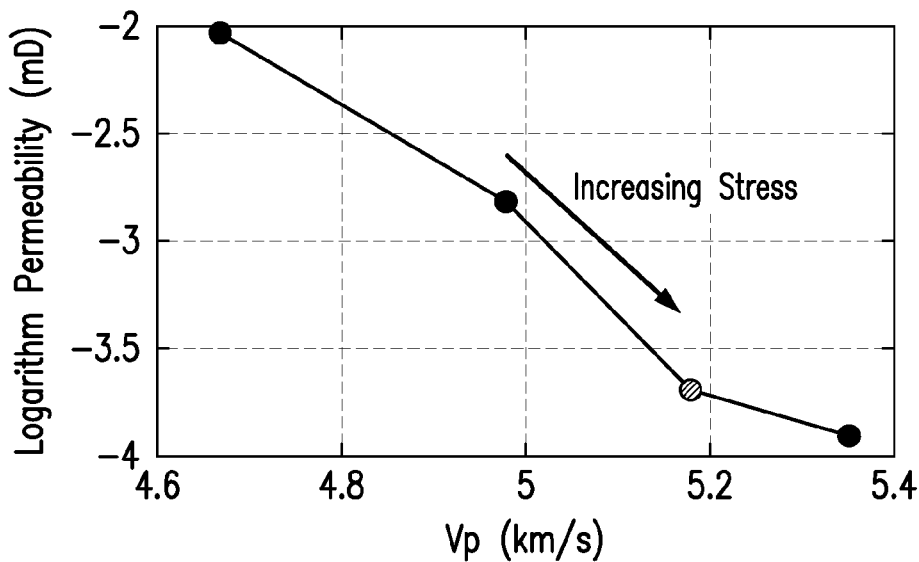
Figure 13A:
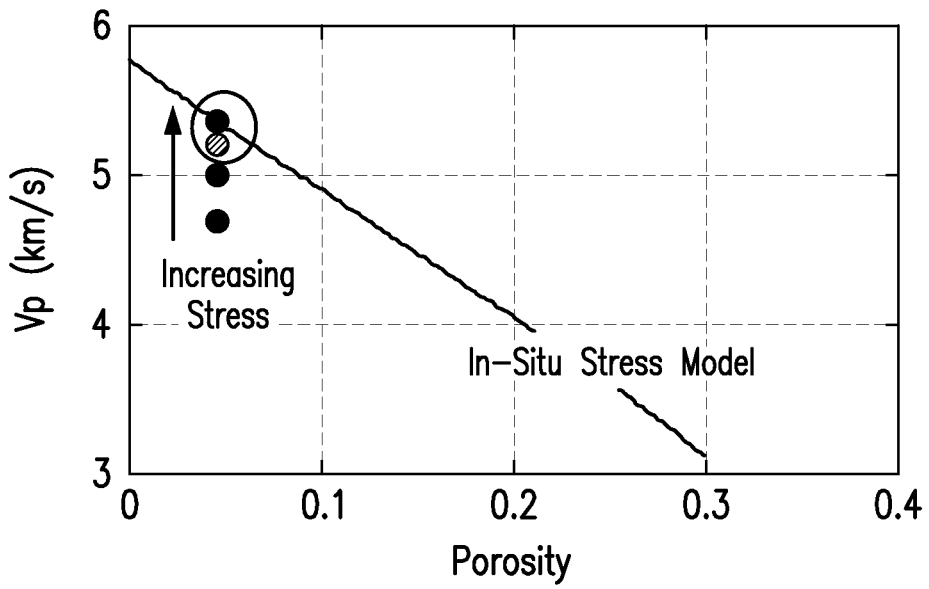
FIGS. 13A-B show plots of P-wave velocity (top) versus porosity in tight gas sandstone at varying stress. These plots use the same data as used in FIGS. 12A-C.
Figure 13B:
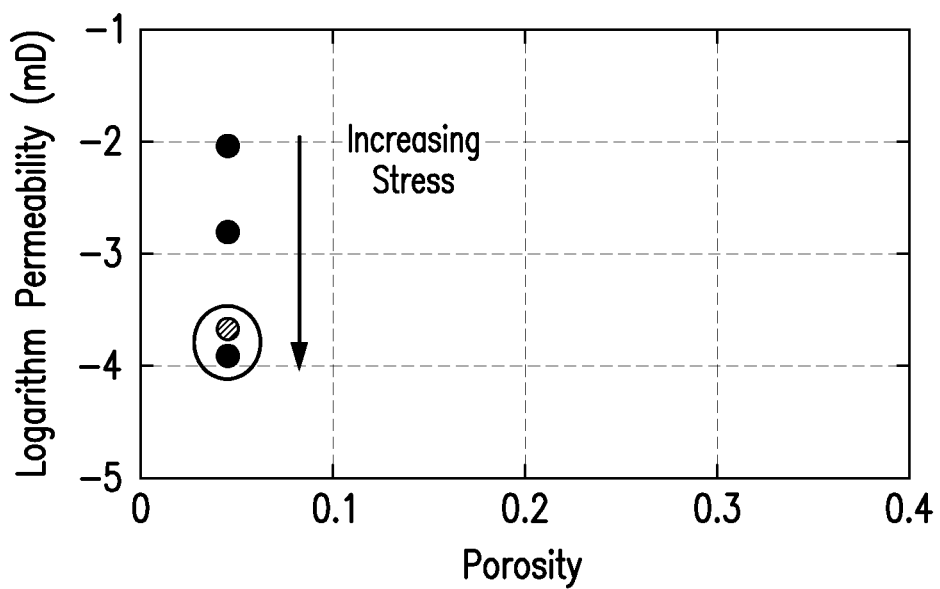

An example of laboratory measurements of the elastic-wave velocity and permeability versus confining stress conducted on a tight gas sandstone sample of about 0.05 porosity is shown in FIGS. 12A-C. Simultaneous increase in the velocity and reduction in permeability is observed as the stress increases from its benchtop value to high value, close to the in-situ stress. It has been deduced from this example that if the measured elastic-wave velocity is close to the expected in-situ-stress value, the permeability measured at the same conditions is also close to the in-situ value. Where velocity and permeability data are obtained on the same sample and at the same stress, but the magnitude of the stress is not registered, then there can be a question on how to determine whether these data are relevant to the in-situ (rather than benchtop) conditions. A resolution has been developed from comprehensive rock physics models that robustly relate the elastic-wave velocity to porosity at in-situ stress conditions. Such models have been developed for the elastic properties, but not permeability per se. Therefore, the velocity can be used as an indicator of stress and propose that if the measured velocity matches the in-situ-stress model, so will the permeability (and other rock properties) if measured concurrently with the velocity. An example of applying such model-based diagnostics to the tight gas sandstone data displayed in FIGS. 12A-C is shown in FIG. 13A where only the upper two velocity data points (at 50 and 100 MPa confining stress) match the velocity-porosity model curve. From this, it can be concluded that only two permeability values concurrent with these two velocity values are relevant to the in-situ conditions (FIG. 13B).

Further, although the rock properties are computed on rock images obtained at benchtop conditions, these images may or may not reveal the very thin cracks that appear in the sample due to confining stress reduction, and a determination is needed on whether the image contains these cracks or not. The answer is similar as for the physical measurement, and the procedure can be as follows:

(a) compare the computed elastic-wave velocity to the relevant in-situ-stress rock physics model velocity-porosity curve, (b) if the computed data match the model, the image reflects the in-situ conditions and, hence, the porosity, permeability, and electrical resistivity computed on this image correspond to in-situ conditions, (c) if the computed velocity data do not match the model, process the image to either remove the cracks (if the computed velocity is smaller than predicted by the model) or introduce the cracks (if the computed velocity is larger than predicted by the model) and re-compute the velocity until a match between the computed and theoretical velocity is obtained (an alternative is to subsample the sample and check whether one or more of the subsamples meet the velocity criterion), and (d) the image thus processed (or a subsample of the image) is relevant to the in-situ conditions and, hence, the porosity, permeability, and electrical conductivity computed on this image are close to their in-situ values.

Finally, the computed velocity data has to be compared to a theoretical curve calculated for the same mineralogical composition as used in these computations. For the purpose of diagnosing whether the rock image under examination is appropriate for computing permeability and electrical resistivity at in-situ conditions, the elastic property computations can be conducted for any mineralogical composition (e.g., pure quartz). These results are then compared to the pure-quartz theoretical curve.

Figure 14:
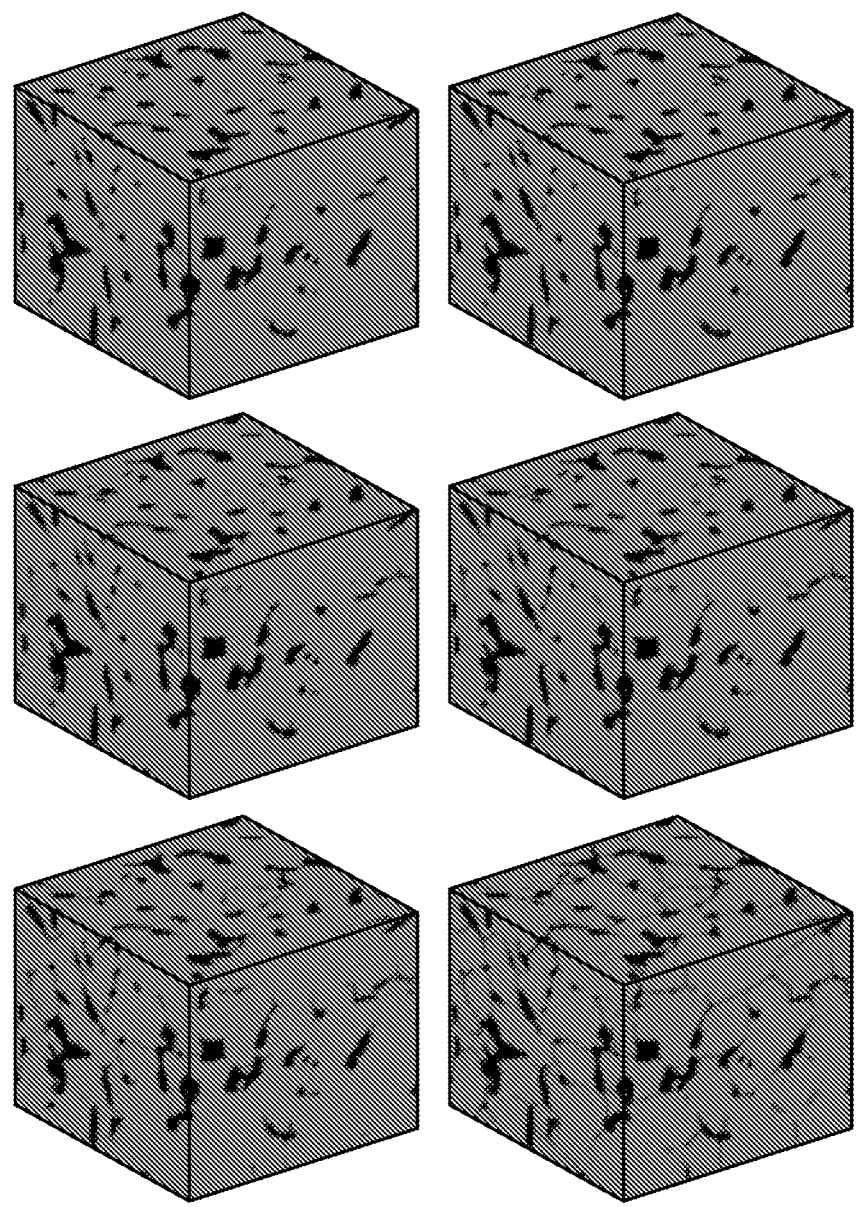
FIG. 14 is a set of digital rock images referred to in an example herein of a method of adjusting a 3D matrix to represent in-situ conditions.
Figure 15A:
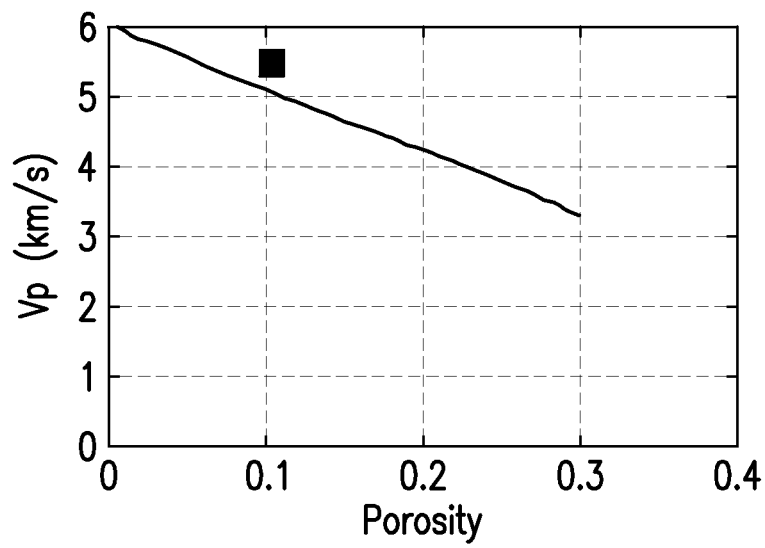
FIGS. 15A-B are plots of P- and S-wave velocity versus porosity as computed for the sample shown in FIG. 14 (top-left). The curve is from the stiff-sand model, and the rock is assumed to be pure quartz.
Figure 15B:
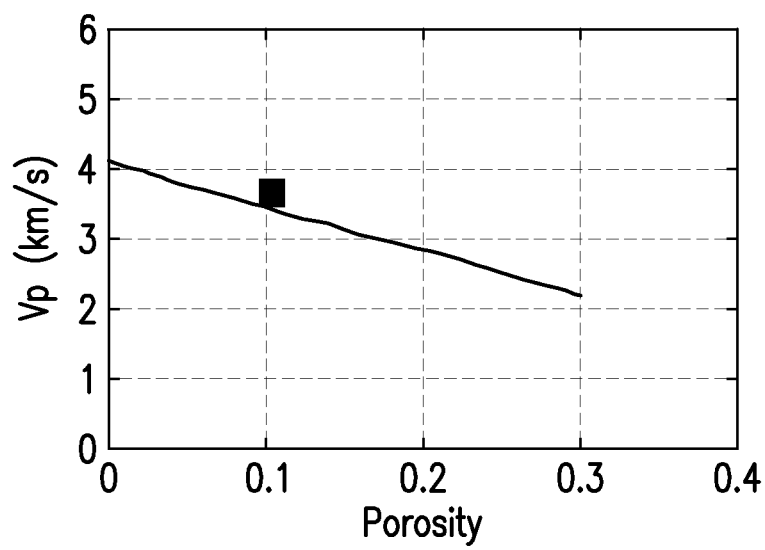
Figure 16B:
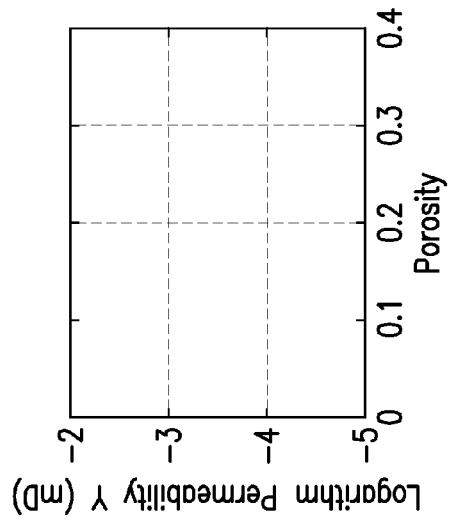
FIGS. 16A-C are plots of permeability (decimal logarithm) versus porosity computed in the x, y, and z directions (left to right) for the same digital sample as used for velocity computations shown in FIGS. 15A-B. The y-direction permeability is zero.
Figure 16C:
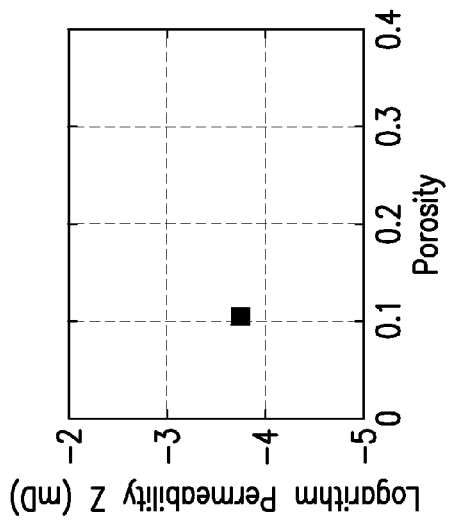
Figure 16A:
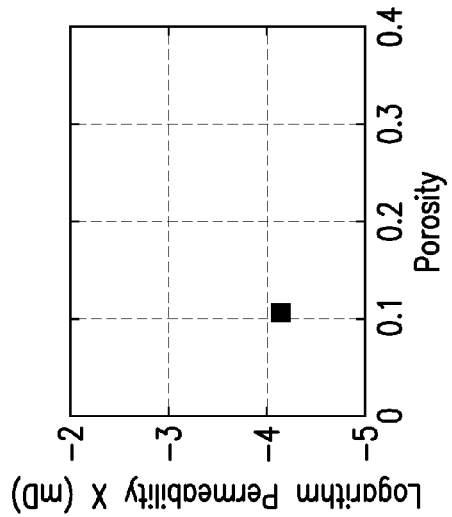

For introducing cracks, a 3D rock image in FIG. 14 (top-left) is shown for sake of illustration. In FIG. 14, the original image is top left, and the other five images show gradual introduction of thin cracks into this image (left to right and top to bottom) to simulate varying state of confining stress. More cracks appear as the stress is reduced. It may be questioned whether the permeability computed on this image is relevant to the in-situ (high confining stress) conditions of the rock. To solve this question, it is assumed that this sample is pure quartz, and its elastic properties are computed and compared to the pure-quartz theoretical curve (FIGS. 15A-B). The directional permeability values computed on the same digital sample are shown in FIGS. 16A-C. As indicated, the y-direction permeability is zero (FIG. 16B).

Figure 17A:
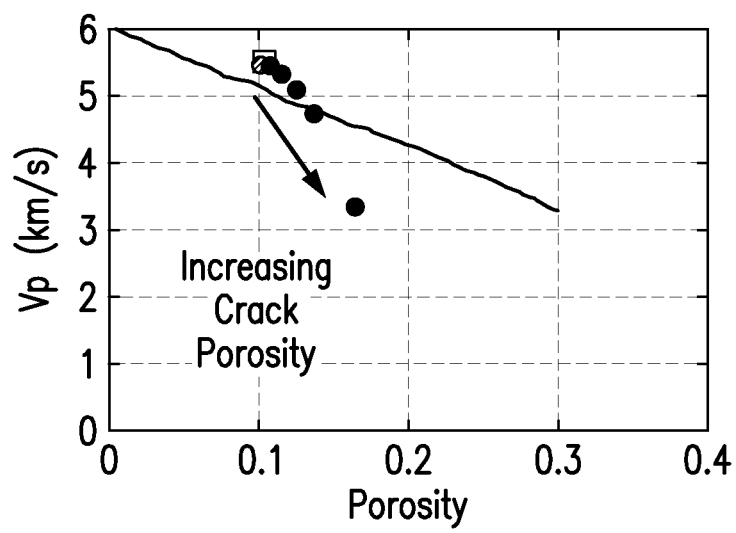
FIGS. 17A-B are plots of P- and S-wave velocity versus porosity as computed for all six samples shown in FIG. 14. The values computed on the original digital sample are squares. The curve is from the stiff-sand model, and the rock is assumed to be pure quartz. The arrows show the direction of increasing crack porosity.
Figure 17B:
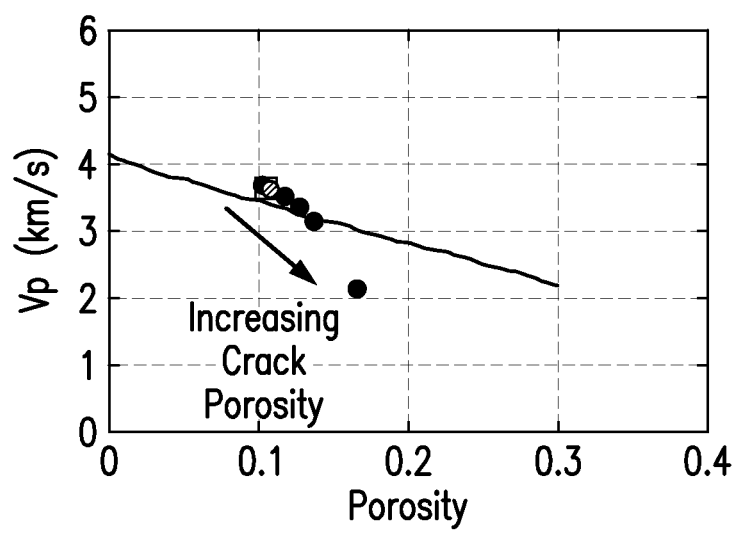
Figure 18A:
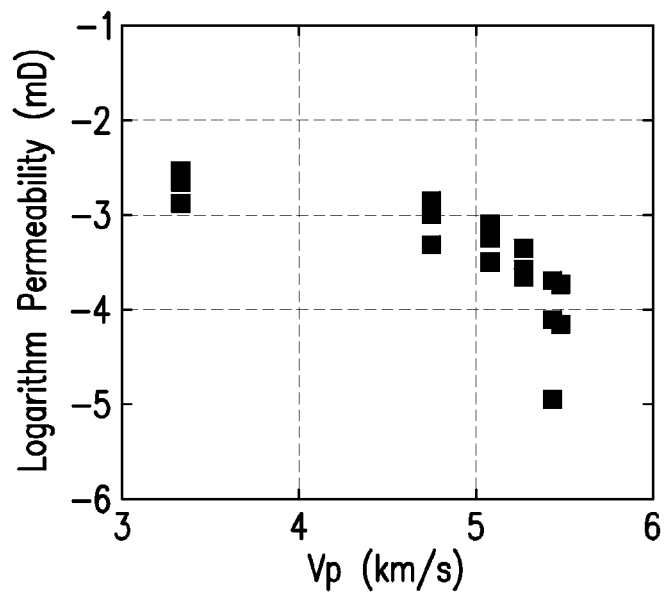
FIGS. 18A-B are plots of decimal logarithm of directional permeability versus the P- (left) and S-wave (right velocity). The digital data are the same as displayed in FIGS. 17A-B. The permeability was computed in three directions. These permeability values are represented by the squares (x), squares (y), and squares (z).
Figure 18B:
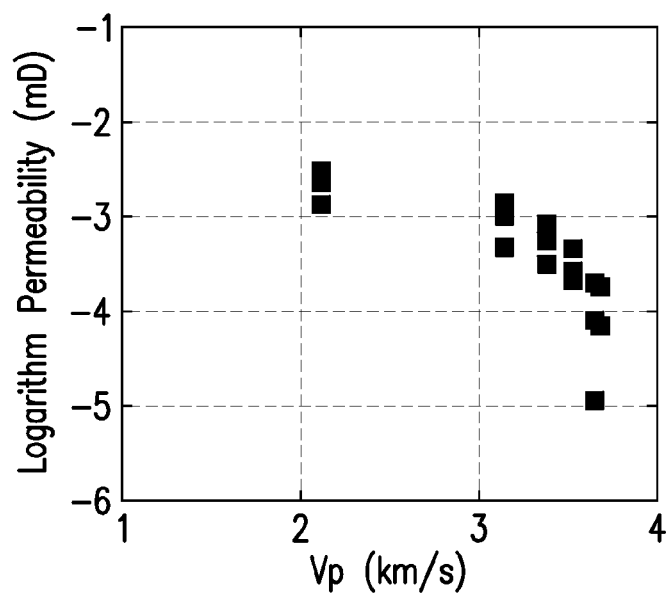

It is clear from FIGS. 15A-B that the computed P- and S-wave velocity values fall above the theoretical curves. This means that some of the thin cracks that exist in-situ were not imaged, likely because the resolution was not fine enough for this purpose. This also means that the permeability computed on the same digital sample may possibly be smaller than in-situ. The next step is to process this original image to introduce the cracks that affect the elastic properties of this sample. The five versions of the new image are shown in FIG. 14 where the crack porosity was gradually increased from zero in the original sample to about 0.06 in the image with pervasive cracks (FIG. 14). As a result, the total porosity of this digital sample increased from 0.105 to 0.165. The P- and S-wave velocity computed on these five samples are plotted versus the total porosity in FIGS. 17A-B. The permeability-velocity plots for these digital data are shown in FIGS. 18A-B. The permeability was computed in three directions (x, y, z). These permeability values are represented by the squares (x)(i.e., the squares having the lowest permeability values for the first four Vp and Vs values (moving left to right in the plots), and the squares having the intermediate permeability values for the highest two Vp and Vs values at the right side of the plots); squares (y) (i.e., the squares having the intermediate permeability values for the first four Vp and Vs values (moving left to right in the plots), and the square having the lowest permeability value for the highest Vp and Vs values at the right side of the plots); and squares (z) (i.e., the squares having the highest permeability values for all the Vp and Vs values (moving left to right in the plots).

Figure 19A:
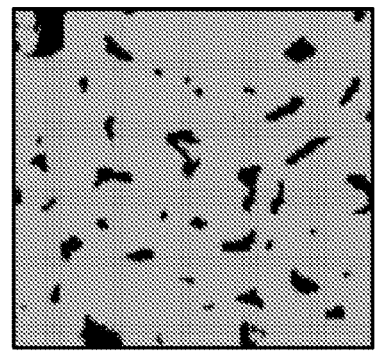
FIGS. 19A-C are a set of digital rock images showing 2D slices of the original digital sample (FIG. 19A) and its two alterations with porosity 0.126 (FIG. 19B) and 0.138 (FIG. 19C), wherein the slices are taken along the same planes in respective 3D images.
Figure 19B:
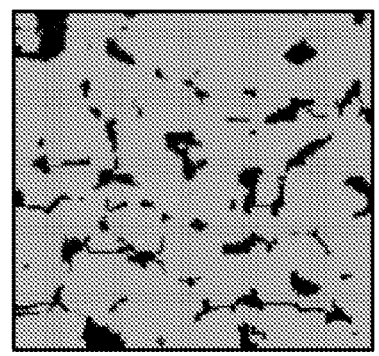
Figure 19C:
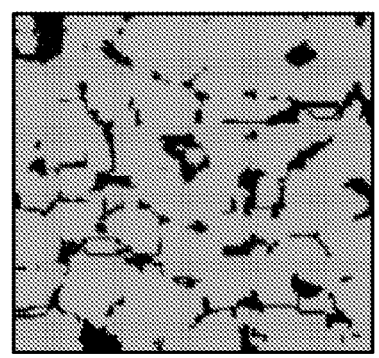

It can be concluded that the directional permeability computed on these two digital samples (FIGS. 19A-C) may fall within the expected in situ range (FIGS. 20A-C). This permeability is about 0.00040 mD in the x direction, 0.00063 mD in the y direction, and 0.00125 mD in the z direction.

On some occasions, the velocity computed on a digital sample may fall below the criterion velocity-porosity curve, as in the tight gas sandstone (TGS) sample with the computed porosity and velocity shown in FIGS. 21A-B. This means that some of the cracks generated due to the unloading of the sample do appear in the image of the sample.

One way of dealing with this situation is to process the original image to close these cracks. Another way is to subsample this sample by, e.g., evenly subdividing it into eight (2×2×2) subsamples (FIG. 22) and compute the porosity and velocity on each of these subsamples with the prospect that some of the results will fall onto the criterion velocity-porosity curve. If so, then the permeability computed on these subsamples can be considered to fall into the in-situ range. If not, techniques can be use to heal the cracks. Image cracks can be closed or healed using the method such as described in U.S. Patent Application Publication No. 2010/0131204 A1, especially the discussion related to FIGS. 12A-12D therein, which is incorporated herein by reference in its entirety. This procedure allows removal of thin cracks, which may have been the result of damage to the rock sample from the drill bit, inelastic stress release and drying.

Figure 21A:
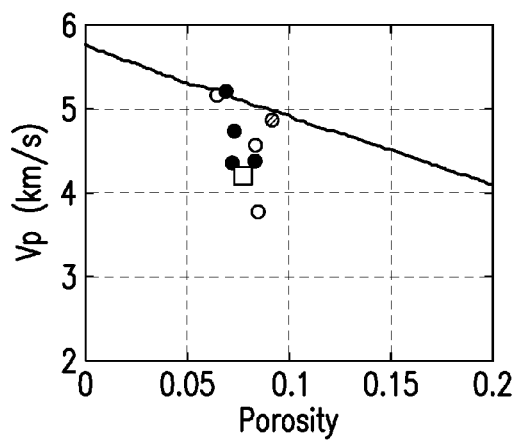
FIGS. 21A-B are plots of P- (left) and S-wave velocity (right) versus porosity in a tight sandstone sample. The gray square is for the data computed on the original sample. The shaded circles are the data computed on the eight subsamples of the original sample. The criterion velocity curve is shown in black.
Figure 21B:
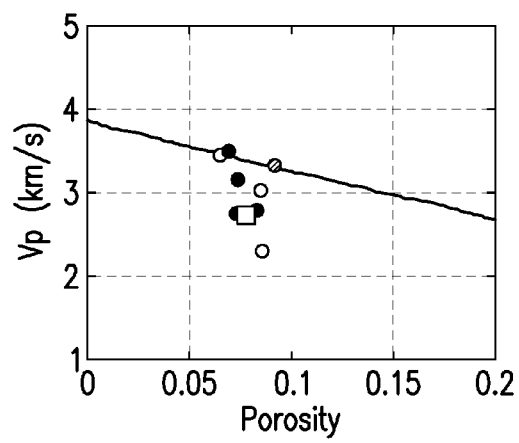
Figure 23A:
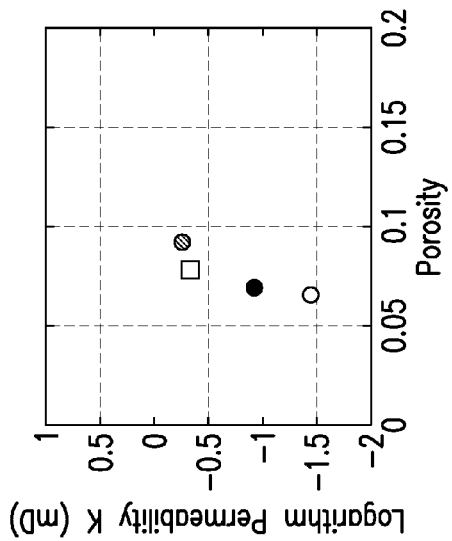
FIG. 23A is a plot of permeability versus porosity computed on the original sample (gray square) and its eight subsamples (colored circles).
Figure 23B:
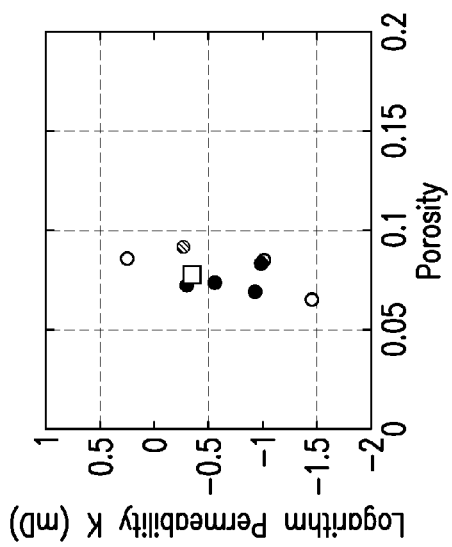
FIG. 23B is a plot similar to FIG. 23A but with data displayed for only three subsamples whose computed P- and S-wave velocity lie close to the criterion curve in FIGS. 21A-B.
Figure 23C:
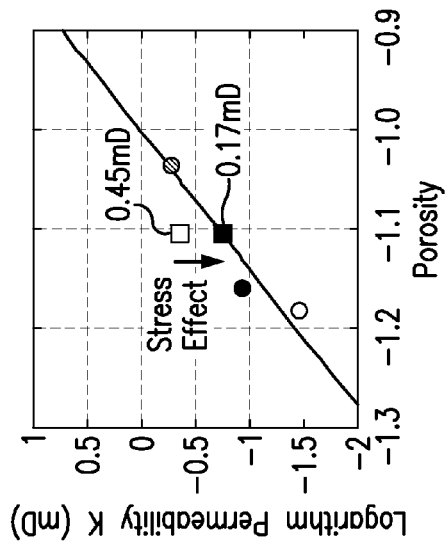
FIG. 23C is a plot similar to FIG. 23B but with decimal logarithm of porosity on the horizontal axis. The black square is the permeability of the original sample adjusted for the in-situ stress, and the line is the best linear fit to the three subsample data points.

The porosity and velocity computed on the eight subsamples of the original TGS sample are displayed in FIGS. 21A-B. Three of these eight data points meet the velocity porosity criterion, and these are the subsamples having data points that fall on the curve shown as a black line. This means that the permeability computed on these three subsamples falls into the in-situ permeability range (FIGS. 23A-C).

The porosities of these three subsamples differ from that of the original sample. To adjust the permeability of the original sample for the in-situ stress conditions, line 11 is fit to the three subsample data points in FIG. 23C and the permeability on this line is computed at the porosity of the original sample. The result is that in the original sample whose computed porosity and permeability (in the x direction) are 0.079 and 0.456 mD, respectively, the permeability adjusted to the in-situ conditions becomes 0.170 mD with a reduction factor about 3.

As demonstrated by these findings, the inability to directly image a rock sample at in-situ stress conditions does not hinder the ability of predicting rock properties at in-situ conditions. This can be accomplished by processing the image and re-computing its physical properties with objective rock physics criteria in mind. The main assumption behind the approach herein is that if one physical attribute of a digital image (the elastic properties) falls within a theoretically established in-situ value range, all other attributes (porosity, permeability, and electrical resistivity) computed on the same image are also expected to fall within the in-situ range.

Step 115

With respect to computational transforms used for the computation engines, the computation transform used can be the Lattice Boltzman method for multiphase fluid simulation, which is a computational transform that can be used to compute transport properties such as absolute and relative permeability. Properties such as viscosity, capillary tension of the fluids, wettability are determined or inferred by the logging tool such as MDT. As indicated, an estimation of relative permeability based only on in-situ fluid composition techniques is indirect. That is, the detailed structure of the formation pore structure would not be known from such downhole logging tool measurements. In the present methods, the rock structure (pores and grains) are input from digital rock physics. Direct calculation of relative permeability is made possible, for example, by applying the Lattice Boltzman numerical method to the 3D pore structure of the formation that is identified within the segmented image of rock and using the pore-fluid properties measured at the interval of investigation by the logging tool.

Figure 24:
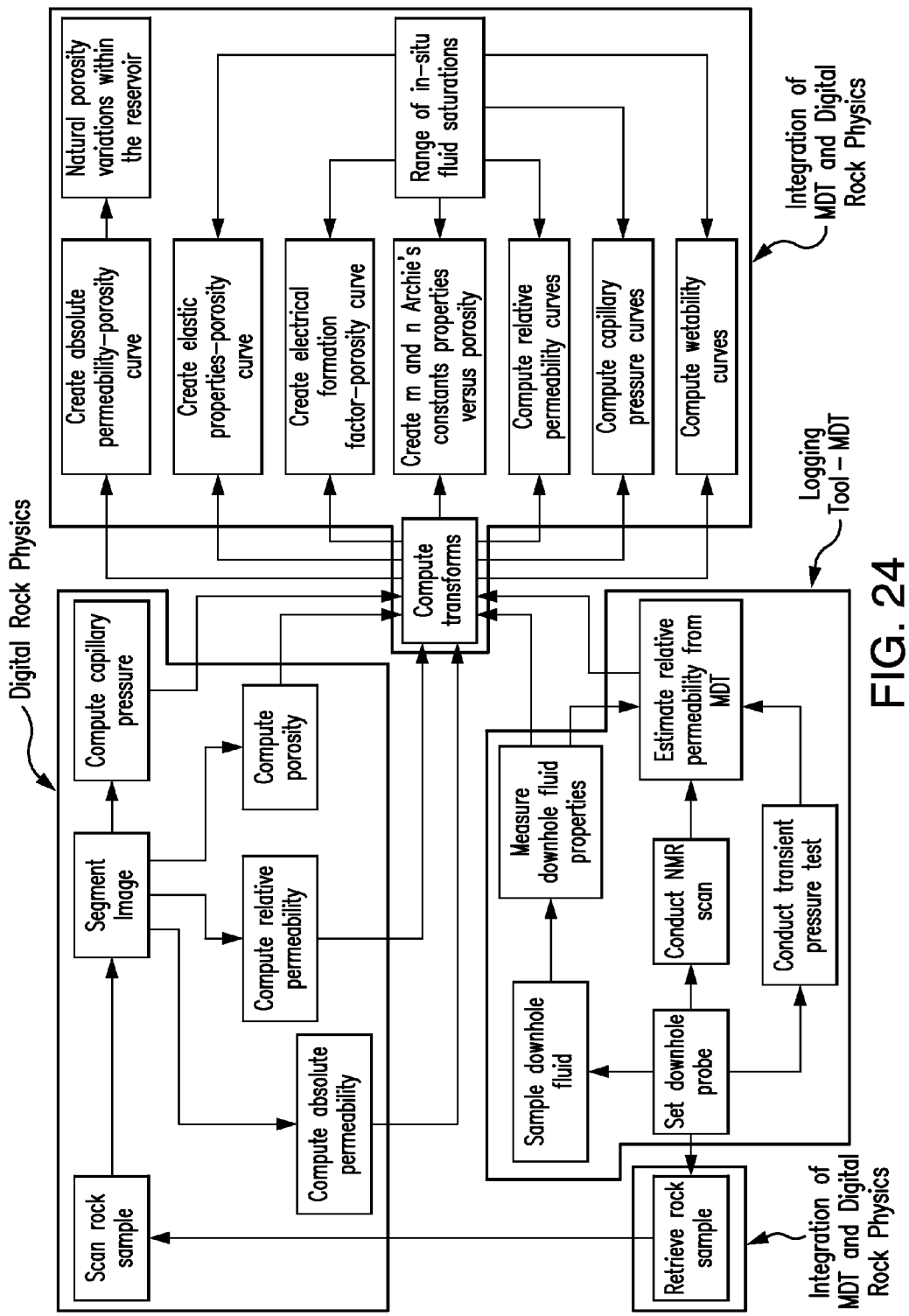
FIG. 24 is a function model of a system and method for integrating well log data and digital rock physics to estimate rock formation properties in accordance with the present invention.

FIG. 24 shows an exemplary workflow for computation of rock properties using properties estimated from well log data and computed from digital rock physics in an integrated manner in accordance with the present invention.

Step 116

The estimated rock properties derived from in situ logging measurements and computed individual rock properties from digital rock physics can be compared in several ways. They can simply be compared, value to value. Several pairs of values from different measurements of the same or different rock locations can be cross plotted. For example, the logging tool estimates may be plotted on the digital trend graph as shown in FIG. 4.

Step 117

The analysis part of step 117 is different from the comparing step 116 in that conclusions or implications are drawn from the comparisons. The quadrant method shown in FIG. 4, for example, is a defined analysis method for this step. It is expected that this area can be further refined as the empirical database is expanded, such as when greater numbers of actual samples are run and comparisons/analyses are performed.

Referring again to FIG. 10, an example of the indicated trend method is shown in more detail. Many of the series 100 steps shown in FIG. 9 are equally applicable to the corresponding series 200 steps of the method shown in FIG. 10 other than steps 213, 217, and 218 in particular. For example, steps 201, 202, 203, 204, 205, 206, 207, 208, 209, 210, 211, 212, 214, 215, and 216 in FIG. 10 can be similar to steps 101, 102, 103, 104, 105, 106, 107, 108, 109, 110, 111, 112, 113, 114, and 115 in FIG. 9, respectively.

Step 213

Figure 3:
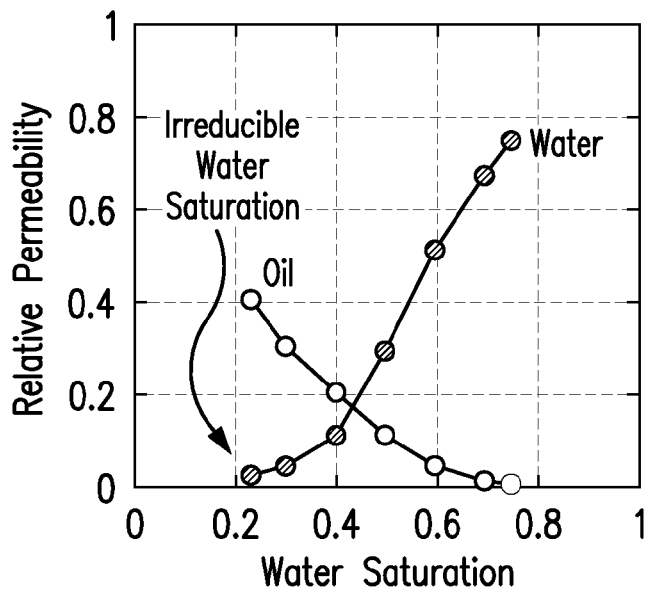
FIG. 3 is a plot showing relative permeability curves where the permeability to oil at the irreducible water saturation is about 40% of the absolute permeability. These curves are obtained from digital rock simulations.
Figure 22:
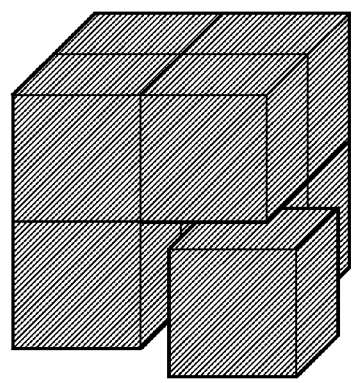
FIG. 22 is a schematical perspective view of an original digital sample divided into subsamples (eight).

To subsample the 3D segmented matrix, a method can be used such as disclosed with respect to FIG. 22, or the methods shown in U.S. Patent Application Publication Nos. 2010/0128932 A1 (e.g., paragraph [0041], FIGS. 3) and 2010/0131204 A1 (e.g., paragraph [0058], FIGS. 7-8), which are incorporated herein by reference in their entireties. For example, to obtain a sufficient number of data points to establish relationships between porosity and other petrophysical parameters, the original segmented image volume may be subdivided into a selected number of sub-volumes, as shown at FIG. 22. Subdividing the image can be performed by dividing the original volume into a number of evenly spaced volumes or by randomly selecting a sufficient number of sub-volumes. One example is to divide a cubic image volume into sub-cubes. Examples of sub-cubes include dividing the original image volume into eight, twenty seven, sixty four or one hundred twenty five cubic sub-volumes. A value of porosity may be determined for each sub-volume.

Step 217

The rock physics relationships can be established by plotting one property versus another, for example, absolute permeability versus porosity.

Step 218

The upscaling can be used to predict rock property relationships outside the range of variation found in the rock sample itself. This is used to produce the trend graph such as shown in FIG. 4.

A program product can be stored on a computer-readable medium, which when executed, enables a computer infrastructure to perform at least steps 114-117 of the point method (e.g., FIG. 9), or at least steps 215-219 of the trend method (e.g., FIG. 10), to integrate individual properties of downhole fluid properties measured or determined and digital rock physics of an earth formation of a reservoir. To this extent, the computer-readable medium includes program code, which implements the process described herein. It is understood that the term "computer-readable medium" comprises one or more of any type of physical embodiment of the program code. In particular, the computer-readable medium can comprise program code embodied on one or more portable storage articles of manufacture (e.g., a compact disc, a memory stick or other portable device, a magnetic disk, a tape, flash memory, etc.), on one or more data storage portions of a computing device, such as memory and/or other storage system, and/or as a data signal traveling over a network (e.g., during a wired/wireless electronic distribution of the program product). To this extent, the deployment of the program product can comprise one or more of: (1) installing program code on a computing device, such as computer 27 (FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention. As used herein, it is understood that the terms "program code" and "computer program code" are synonymous and mean any expression, in any language, code, or notation, of a set of instructions that cause a computing device having an information processing capability to perform a particular function either directly or after any combination of the following: (a) conversion to another language, code or notation; (b) reproduction in a different material form; and/or (c) decompression. To this extent, program code can be embodied as one or more types of program products, such as an application/software program, component software/a library of functions, an operating system, a basic I/O system/driver for a particular computing and/or I/O device, and the like. Further, it is understood that the terms "component" and "system" are synonymous as used herein and represent any combination of hardware and/or software capable of performing some function(s).

The present invention includes the following aspects/embodiments/features in any order and/or in any combination:

1. The present invention relates to a method for making estimates of subterranean rock properties, comprising
    a) positioning a logging tool inside a well bore,
    b) measuring in situ fluid properties in at least one well interval in a well using the logging tool,
    c) measuring in situ well properties in the well interval in the well using the logging tool,
    d) estimating rock properties in the well for a location of the logging tool in the well interval using the measured in situ well properties,
    e) retrieving at least one rock sample from the well interval in the well,
    f) preparing said at least one rock sample for digital rock physics analysis,
    g) scanning the at least one rock sample to produce a digital image of said rock sample,
    h) segmenting said digital image of said rock sample to define pores and grains in said digital image,
    i) adjusting said digital image to represent said rock properties at in-situ conditions using said well properties,
    j) calculating rock properties from said adjusted digital image of said rock sample using said in situ fluid properties, and
    k) comparing said rock properties at the well interval where the logging tool was positioned and said rock properties from said digital image of said rock sample using said in situ fluid properties.

2. The method of any preceding or following embodiment/feature/aspect, further comprising l) at least one of storing, displaying, and printing results of said comparing.

3. The method of any preceding or following embodiment/feature/aspect, further comprising m) extracting at least one of fluid and gaseous contents of a subsurface reservoir at or adjacent said well interval based on results of said comparing.

4. The method of any preceding or following embodiment/feature/aspect, wherein said rock sample is produced by rotary core, percussion, or combinations thereof.

5. The method of any preceding or following embodiment/feature/aspect, wherein said fluid properties are temperature, pressure, viscosity, chemical composition, or any combination thereof.

6. The method of any preceding or following embodiment/feature/aspect, wherein said in situ well properties are downhole images, well bore gauge, temperature, pressure, resistivity, gamma, neutron-density, T1 and T2 relaxation times from NMR, or any combination thereof.

7. The method of any preceding or following embodiment/feature/aspect, wherein said rock properties comprise absolute permeability, total porosity, connected porosity, relative permeability, capillary pressure, m and n Archies constants, elastic moduli, or electrical properties, or any combinations thereof.

8. The method of any preceding or following embodiment/feature/aspect, further comprising conducting an in situ pressure transient test during the well interval.

9. The method of any preceding or following embodiment/feature/aspect, further comprising a digital simulation of said in situ pressure transient test.

10. The method of any preceding or following embodiment/feature/aspect, further comprising a comparison of said in situ pressure transient test and said digital simulation of said in situ pressure transient test.

11. The method of any preceding or following embodiment/feature/aspect, wherein said rock sample has a diameter size of about 2 cm or less and a length of about 2 cm or less.

12. The method of any preceding or following embodiment/feature/aspect, wherein step k) comprises comparing (i) a logging tool data point plotted as absolute permeability versus porosity for the rock properties estimated from the in situ well properties measured with the logging tool in the well interval, with (ii) digital rock physics data points plotted as absolute permeability versus porosity for the rock properties calculated from said adjusted digital images, and selecting the digital rock physics data point which is closest to the logging tool data point, and further comprising l) using the selected digital rock physics point in at least one subsequent digital rock physics calculation.

13. A method for estimating subterranean rock properties of a rock formation comprising
   a) positioning a logging tool at more than one location inside a well bore,
   b) measuring in situ fluid properties in a well using a logging tool at said more than one location,
   c) measuring in situ well properties at said more than one location,
   d) estimating rock properties in the well at said more than one location,
   e) retrieving rock samples from approximately each of said more than one locations,
   f) preparing said rock samples for digital rock physics analysis,
   g) scanning said rock samples to produce digital images of said rock samples,
   h) subdividing said digital images into 8 or more digital sub-images,
   i) segmenting said digital sub-images to define pores and grains in said digital sub-images,
   j) adjusting said digital sub-images to represent said rock properties at in situ conditions using said well properties,
   k) establishing rock physics relations comprising trends, transforms, models, or any combinations thereof,
   l) expanding said rock physics relations beyond the range of parameters measured in said trends, transforms, models or any combinations thereof,
   m) comparing said rock properties in the well approximately at the more than one location of the logging tool and said rock properties from said digital image of said rock sample using said in situ fluid properties,
   n) selecting one or more rock properties measured in the well or core sample, and
   o) reconstructing additional rock properties by applying said rock physics relations trends, transforms and models to said one or more rock properties measured in the well or core sample.

14. The method of any preceding or following embodiment/feature/aspect, wherein said rock sample is produced by rotary core or percussion.

15. The method of any preceding or following embodiment/feature/aspect, wherein said fluid properties comprise temperature, pressure, viscosity, chemical composition, or any combinations thereof.

16. The method of any preceding or following embodiment/feature/aspect, wherein said in situ well properties comprise downhole images, well bore gauge, temperature, pressure, resistivity, gamma, neutron-density, T1 and T2 relaxation times from NMR, or any combinations thereof.

17. The method of any preceding or following embodiment/feature/aspect, wherein said rock properties comprise absolute permeability, total porosity, connected porosity, relative permeability, capillary pressure, m and n Archies constants, elastic moduli, electrical properties, or any combinations thereof.

18. The method of any preceding or following embodiment/feature/aspect, wherein said rock physics relations comprise at least one relationship between velocity, porosity, and mineralogy; permeability, porosity, and mineralogy; electrical formation factor, porosity and mineralogy; and relative permeability and saturation.

19. The method of any preceding or following embodiment/feature/aspect, wherein said rock sample has a diameter size of about 2 cm or less or a length of about 2 cm or less.

20. A system for making estimates of subterranean rock properties, comprising
   a) a logging tool positionable inside a well borehole and operable for measuring in situ fluid and well properties in at least one well interval in a well,
   b) at least one computer processor programmable for estimating rock properties in the well for a location of the logging tool in the well interval using the measured in situ well properties,
   c) a sampling tool operable for retrieving at least one rock sample from a rock formation bounding the well borehole in the well interval, and
   d) a CT or SEM scanner operable to produce digital images of at least one retrieved rock sample from the formation, and
   e) at least one computer processor programmable for segmenting said digital images of said rock sample to define pores and grains in said digital image, adjusting said digital image to represent said rock properties at in-situ conditions using said well properties, calculating rock properties from said adjusted digital image of said rock sample using said in situ fluid properties, and comparing said rock properties at the well interval where the logging tool being positionable and said rock properties from said digital image of said rock sample using said in situ fluid properties.

21. The system of any preceding or following embodiment/feature/aspect, wherein the logging tool comprises an MDT tool and the sampling tool comprises a sidewall rotary coring tool.

22. A computer program product on a computer readable medium that, when performed on a processor in a computerized device provides a method for performing computations of at least one of steps (h), (i), (j), and (k) of claim 1.

The present invention can include any combination of these various features or embodiments above and/or below as set forth in sentences and/or paragraphs. Any combination of disclosed features herein is considered part of the present invention and no limitation is intended with respect to combinable features.

EXAMPLES

Example 1

An example of rebuilding the physical properties of rock of a well interval, such as from core or drill cuttings retrieved from the interval of interest, is the following.

1. Collect a number of relatively large (~1 mm) cuttings or core samples from the interval of interest where logging has been conducted or a core extracted.

2. Produce a CT Image of the cuttings and segment these images.

3. Bring these images to in-situ conditions.

4. By sub-sampling the resulting digital volumes, establish rock physics relations (trends, transforms, or models) between velocity, porosity, and mineralogy; permeability, porosity, and mineralogy; electrical formation factor versus porosity and mineralogy; relative permeability and saturation. Theoretically substantiate and expand these models.

5. Select one or more of parameters measured in the well (e.g., the bulk density and/or elastic-wave velocity) or on the core (the bulk density and electronic number) and then, by applying the rock physics relations established on the cuttings or core samples, reconstruct (rebuild) the full suite of the physical properties of the logged interval or extracted core.

Following is an example of populating the subsurface with rock properties not directly measured in-situ for seismic interpretation.

1. Rock physics relations (trends, transforms, or models) are established by combining a set of controlled experiments and rock physics theory. These controlled experiments are conducted in the computational rock physics laboratory on a set of drill cuttings.

2. The rock physics relations (trends) are established and upscaled. Then these upscaled relations are applied to the elastic properties inferred from seismic data to populate the seismic volumes of interest with the missing properties.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for making estimates of subterranean rock properties, comprising:
    a) positioning a logging tool inside a well bore,
    c) measuring in situ well properties in the well interval in the well using the logging tool,
    d) estimating rock properties in the well for a location of the logging tool in the well interval using the measured in situ well properties,
    e) retrieving at least one rock sample from the well interval in the well,
    f) preparing said at least one rock sample for digital rock physics analysis,
    g) scanning the at least one rock sample to produce a digital image of said rock sample,
    h) segmenting said digital image of said rock sample to define pores and grains in said digital image,
    i) adjusting said digital image to represent said rock properties at in-situ conditions using said well properties,
    j) calculating rock properties from said adjusted digital image of said rock sample using said in situ fluid properties,
    k) comparing said rock properties at the well interval where the logging tool was positioned and said rock properties from said digital image of said rock sample using said in situ fluid properties,
    l) positioning a logging tool inside a well bore of a similar formation as that of the wellbore of step a),
    m) repeating step c) for measuring in situ well properties using the logging tool used in step l),
    n) estimating rock properties in the well for a location of the logging tool used in step l) in a well interval using the measured in situ well properties from step m), and
    o) correcting the estimates of rock properties from step n) during the logging process using rock properties or rock property trends determined from said adjusted digital image in step j).

2. The method of claim 1, further comprising: conducting an in situ pressure transient test during the well interval.

3. The method of claim 2, further comprising: a digital simulation of said in situ pressure transient test.

4. The method of claim 2, further comprising: a comparison of said in situ pressure transient test and said digital simulation of said in situ pressure transient test.

5. The method of claim 1, further comprising: l) at least one of storing, displaying, and printing results of said comparing.

6. The method of claim 5, further comprising: m) extracting at least one of fluid and gaseous contents of a subsurface reservoir at or adjacent said well interval based on results of said comparing.

7. The method of claim 1, wherein said rock sample is produced by rotary core, percussion, or combinations thereof.

8. The method of claim 1, wherein said in situ well properties are downhole images, well bore gauge, temperature, pressure, resistivity, gamma, neutron-density, T1 and T2 relaxation times from NMR, or any combination thereof.

9. The method of claim 1, wherein said rock properties comprise absolute permeability, total porosity, connected porosity, relative permeability, capillary pressure, m and n Archies constants, elastic moduli, or electrical properties, or any combinations thereof.

10. The method of claim 1, wherein said rock sample has a diameter size of about 2 cm or less and a length of about 2 cm or less.

11. The method of claim 1, wherein step k) comprises comparing (i) a logging tool data point plotted as absolute permeability versus porosity for the rock properties estimated from the in situ well properties measured with the logging tool in the well interval, with (ii) digital rock physics data points plotted as absolute permeability versus porosity for the rock properties calculated from said adjusted digital images, and selecting the digital rock physics data point which is closest to the logging tool data point, and further comprising using the selected digital rock physics point in at least one subsequent digital rock physics calculation.

12. A computer program product on a non-transitory computer readable medium that, when performed on a processor in a computerized device provides a method for performing computations of steps (h), (i), (j), (k), and (o) of claim 1.

13. A method for estimating subterranean rock properties of a rock formation comprising:
    a) positioning a logging tool at more than one location inside a well bore,
    b) measuring in situ fluid properties in a well using a logging tool at said more than one location, wherein said in situ fluid properties comprise temperature, pressure, viscosity, chemical composition, fluid compressibility, or density, or any combinations thereof,
    c) measuring in situ well properties at said more than one location, d) estimating rock properties in the well at said more than one location,
e) retrieving rock samples from approximately each of said more than one locations,
f) preparing said rock samples for digital rock physics analysis,
g) scanning said rock samples to produce digital images of said rock samples,
h) subdividing said digital images into 8 or more digital sub-images,
i) segmenting said digital sub-images to define pores and grains in said digital sub-images,
j) adjusting said digital sub-images to represent said rock properties at in situ conditions using said well properties and calculating rock properties from said adjusted digital sub-images of said rock sample using said in situ fluid properties,
k) establishing rock physics relations comprising trends, transforms, models, or any combinations thereof,
l) expanding said rock physics relations beyond the range of parameters measured in said trends, transforms, models or any combinations thereof,
m) comparing said rock properties in the well approximately at the more than one location of the logging tool and said rock properties from said adjusted digital sub-images of said rock sample using said in situ fluid properties,
n) selecting one or more rock properties measured in the well or core sample,
o) reconstructing additional rock properties by applying said rock physics relations trends, transforms and models to said one or more rock properties measured in the well or core sample,
p) positioning a logging tool inside a well bore of a similar formation as that of the wellbore of step a),
q) repeating step c) for measuring in situ well properties using the logging tool used in step p),
r) estimating rock properties in the well for a location of the logging tool used in step p) in a well interval using the measured in situ well properties from step q), and
s) correcting the estimates of rock properties from step r) during the logging process using rock properties or rock property trends determined from said adjusted digital image in step j).

14. The method of claim 13, wherein said rock sample is produced by rotary core or percussion.

15. The method of claim 13, wherein said in situ well properties comprise downhole images, well bore gauge, temperature, pressure, resistivity, gamma, neutron-density, T1 and T2 relaxation times from NMR, or any combinations thereof.

16. The method of claim 13, wherein said rock properties comprise absolute permeability, total porosity, connected porosity, relative permeability, capillary pressure, m and n Archies constants, elastic moduli, electrical properties, or any combinations thereof.

17. The method of claim 13, wherein said rock physics relations comprise at least one relationship between velocity, porosity, and mineralogy; permeability, porosity, and mineralogy; electrical formation factor, porosity and mineralogy; and relative permeability and saturation.

18. The method of claim 13, wherein said rock sample has a diameter size of about 2 cm or less or a length of about 2 cm or less.

19. A system for making estimates of subterranean rock properties, comprising:
a) a logging tool positionable inside well boreholes of similar formation and operable for measuring in situ fluid properties and well properties in at least one well interval in a well, wherein said in situ fluid properties comprise temperature, pressure, viscosity, chemical composition, fluid compressibility, or density, or any combinations thereof,
b) at least one computer processor programmable for estimating rock properties in the well for a location of the logging tool in the well interval using the measured in situ well properties,
c) a sampling tool operable for retrieving at least one rock sample from a rock formation bounding the well borehole in the well interval, and
d) a (computer tomographic) CT or (scanning electron microscope) SEM scanner operable to produce digital images of at least one retrieved rock sample from the formation, and
e) at least one computer processor programmable for segmenting said digital images of said rock sample to define pores and grains in said digital image, adjusting said digital image to represent said rock properties at in-situ conditions using said well properties, calculating rock properties from said adjusted digital image of said rock sample using said in situ fluid properties, comparing said rock properties at the well interval where the logging tool being positionable and said rock properties from said adjusted digital image of said rock sample using said in situ fluid properties, and comparing additional rock properties at a well interval where a logging tool being positionable in a similar formation and said rock properties from said adjusted digital image of said rock sample using said in situ fluid properties for correcting the additional rock properties.

20. The system of claim 19, wherein the logging tool comprises a modular formation dynamics tester (MDT) tool and the sampling tool comprises a sidewall rotary coring tool.

* * * * *

UNITED STATES PATENT AND TRADEMARK OFFICE
CERTIFICATE OF CORRECTION

Page 1 of 1

PATENT NO.      : 9,507,047 B1
APPLICATION NO. : 13/465105
DATED           : November 29, 2016
INVENTOR(S)     : Dvorkin et al.

It is certified that error appears in the above-identified patent and that said Letters Patent is hereby corrected as shown below:

In the Claims

In Claim 1, Column 37, Lines 44 - 46:
"a) positioning a logging tool inside a well bore,
c) measuring in situ well properties in the well interval in the well using the logging tool,"

should read:
-- a) positioning a logging tool inside a well bore,
b) measuring in situ fluid properties in at least one well interval in a well using the logging tool, wherein said in situ fluid properties are temperature, pressure, viscosity, chemical composition, fluid compressibility, or density, or any combination thereof,
c) measuring in situ well properties in the well interval in the well using the logging tool, --

Signed and Sealed this
Twenty-fourth Day of January, 2017

Michelle K. Lee
*Director of the United States Patent and Trademark Office*